(12) United States Patent
Martin et al.

(10) Patent No.: US 6,361,637 B2
(45) Date of Patent: *Mar. 26, 2002

(54) METHOD OF MAKING A KINK RESISTANT STENT-GRAFT

(75) Inventors: Gerald Ray Martin, Flagstaff, AZ (US); Lilip Lau, Sunnyvale, CA (US); Scott N. Stonebrook, Flagstaff, AZ (US); Sharon Lam, Redwood City; Troy Thornton, San Francisco, both of CA (US)

(73) Assignee: Gore Enterprise Holdings, Inc., Newark, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/376,931

(22) Filed: Aug. 13, 1999

Related U.S. Application Data

(60) Division of application No. 08/896,805, filed on Jul. 18, 1997, now Pat. No. 6,042,605, which is a continuation-in-part of application No. 08/572,548, filed on Dec. 14, 1995, now abandoned.

(51) Int. Cl.[7] .................................................. A61F 2/06
(52) U.S. Cl. ........................ 156/187; 156/191; 156/192; 156/308.2; 623/1.13
(58) Field of Search ........................ 623/1.13; 156/187, 156/191, 192, 308.2

(56) References Cited

U.S. PATENT DOCUMENTS

| | | |
|---|---|---|
| 2,638,093 A | 5/1953 | Kulick |
| 3,029,819 A | 4/1962 | Starks |
| 3,096,560 A | 7/1963 | Liebig |
| 3,142,067 A | 7/1964 | Liebig |
| 3,152,618 A | 10/1964 | Rothermel et al. |
| 3,174,851 A | 3/1965 | Buehler et al. |
| 3,351,463 A | 11/1967 | Rozner et al. |
| 3,479,670 A | 11/1969 | Medell |

(List continued on next page.)

FOREIGN PATENT DOCUMENTS

| | | |
|---|---|---|
| AU | 42485/89 | 4/1990 |
| AU | 34742/93 | 1/1993 |
| CA | 2026604 | 4/1991 |
| CA | 2079417 | 4/1993 |

(List continued on next page.)

OTHER PUBLICATIONS

Cragg, et al: *Percutaneous Femoropopliteal Graft Placement*; J. Vascular and Interventional Radiology; pp. 455–462; Jul.–Aug. 1993; vol. 4, No. 4.

(List continued on next page.)

*Primary Examiner*—Jeff H. Aftergut
(74) *Attorney, Agent, or Firm*—Morgan & Finnegan, LLP

(57) ABSTRACT

A stent-graft including a stent member having an inner surface and an outer surface, a generally tubular graft member and a coupling member that couples the stent member to the graft member. The coupling member, which is the preferred embodiment is in the form of a ribbon, covers only a portion of the inner or outer surface of the stent member and secures the stent member and graft member to one another. Alternatively, the coupling member can be to described as interconnecting less than entirely the inner or outer surface of the graft member to the stent member. With this construction, regions of the stent member do not interfere with the coupling member. Shear stresses between the stent member and the coupling member and the risk of tearing the graft or coupling member or delamination therebetween may be reduced as compared to a fully enveloped stent member. This construction also provides improved flexibility and kink resistance.

10 Claims, 19 Drawing Sheets

U.S. PATENT DOCUMENTS

| | | |
|---|---|---|
| 3,514,791 A | 6/1970 | Sparks |
| 3,562,820 A | 2/1971 | Braun |
| 3,625,198 A | 12/1971 | Sparks |
| 3,657,744 A | 4/1972 | Ersek |
| 3,710,777 A | 1/1973 | Sparks |
| 3,753,700 A | 8/1973 | Harrison et al. |
| 3,774,596 A | 11/1973 | Cook |
| 3,805,301 A | 4/1974 | Liebig |
| 3,866,247 A | 2/1975 | Sparks |
| 3,866,609 A | 2/1975 | Sparks |
| 3,868,956 A | 3/1975 | Alfidi et al. |
| 3,927,422 A | 12/1975 | Sawyer |
| 3,938,524 A | 2/1976 | Sparks et al. |
| 3,949,073 A | 4/1976 | Daniels et al. |
| 3,953,566 A | 4/1976 | Gore |
| 3,974,526 A | 8/1976 | Dardik et al. |
| 3,993,045 A | 11/1976 | Ion |
| 4,011,861 A | 3/1977 | Enger |
| 4,047,252 A | 9/1977 | Liebig et al. |
| 4,130,904 A | 12/1978 | Whalen |
| 4,140,126 A | 2/1979 | Choudhury |
| 4,164,045 A | 8/1979 | Bokros et al. |
| 4,187,390 A | 2/1980 | Gore |
| 4,300,244 A | 11/1981 | Bokros |
| 4,306,318 A | 12/1981 | Mano et al. |
| 4,319,363 A | 3/1982 | Ketharanathan |
| 4,355,426 A | 10/1982 | MacGregor |
| 4,411,655 A | 10/1983 | Schreck |
| 4,424,208 A | 1/1984 | Wallace et al. |
| 4,425,908 A | 1/1984 | Simon |
| 4,488,911 A | 12/1984 | Luck et al. |
| 4,494,531 A | 1/1985 | Gianturco |
| 4,502,159 A | 3/1985 | Woodroff et al. |
| 4,503,569 A | 3/1985 | Dotter |
| 4,512,338 A | 4/1985 | Balko et al. |
| 4,517,687 A | 5/1985 | Liebig et al. |
| 4,530,113 A | 7/1985 | Matterson |
| 4,546,500 A | 10/1985 | Bell |
| 4,553,545 A | 11/1985 | Maass et al. |
| 4,557,764 A | 12/1985 | Chu |
| 4,562,596 A | 1/1986 | Kornberg |
| 4,580,568 A | 4/1986 | Gianturco |
| 4,582,640 A | 4/1986 | Smestad et al. |
| 4,592,754 A | 6/1986 | Gupte et al. |
| 4,604,762 A | 8/1986 | Robinson |
| 4,617,932 A | 10/1986 | Kornberg |
| 4,629,458 A | 12/1986 | Pinchuk |
| 4,641,653 A | 2/1987 | Rockey |
| 4,642,117 A | 2/1987 | Nguyen et al. |
| 4,647,416 A | 3/1987 | Seiler, Jr. et al. |
| 4,649,922 A | 3/1987 | Wiktor |
| 4,655,771 A | 4/1987 | Wallsten |
| 4,665,906 A | 5/1987 | Jervis |
| 4,689,399 A | 8/1987 | Chu |
| 4,728,328 A | 3/1988 | Hughes et al. |
| 4,733,665 A | 3/1988 | Palmaz |
| 4,738,666 A | 4/1988 | Fuqua |
| 4,739,762 A | 4/1988 | Palmaz |
| 4,740,207 A | 4/1988 | Kreamer |
| 4,760,849 A | 8/1988 | Kropf |
| 4,776,337 A | 10/1988 | Palmaz |
| 4,787,899 A | 11/1988 | Lazarus |
| 4,790,313 A | 12/1988 | Borrelly |
| 4,795,458 A | 1/1989 | Regan |
| 4,798,606 A | 1/1989 | Pinchuk |
| 4,800,882 A | 1/1989 | Gianturco |
| 4,816,028 A | 3/1989 | Kapadia et al. |
| 4,816,339 A | 3/1989 | Tu et al. |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,856,516 A | 8/1989 | Hillstead |
| 4,877,025 A | 10/1989 | Hanson |
| 4,878,906 A | 11/1989 | Lindemann et al. |
| 4,886,062 A | 12/1989 | Wiktor |
| 4,886,500 A | 12/1989 | Lazarus |
| 4,892,539 A | 1/1990 | Koch |
| 4,913,141 A | 4/1990 | Hillstead |
| 4,921,479 A | 5/1990 | Grayzel |
| 4,941,870 A | 7/1990 | Okada et al. |
| 4,950,227 A | 8/1990 | Savin et al. |
| 4,955,899 A | 9/1990 | Corna et al. |
| 4,957,504 A | 9/1990 | Chardack |
| 4,957,508 A | 9/1990 | Kaneko et al. |
| 4,969,458 A | 11/1990 | Wiktor |
| 4,990,151 A | 2/1991 | Wallsten |
| 4,990,155 A | 2/1991 | Wilkoff |
| 4,994,071 A | 2/1991 | MacGregor |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,035,706 A | 7/1991 | Gianturco et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,042,161 A | 8/1991 | Hodge |
| 5,064,435 A | 11/1991 | Porter |
| 5,066,298 A | 11/1991 | Hess |
| 5,067,957 A | 11/1991 | Jervis |
| 5,078,726 A | 1/1992 | Kreamer |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,424 A | 4/1992 | Hoffman, Jr. et al. |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,139,480 A | 8/1992 | Hickle et al. |
| 5,147,370 A | 9/1992 | McNamara et al. |
| 5,151,105 A | 9/1992 | Kwan-Gett |
| 5,156,619 A | 10/1992 | Ehrenfeld |
| 5,161,547 A | 11/1992 | Tower |
| 5,162,430 A | 11/1992 | Rhee et al. |
| 5,163,958 A | 11/1992 | Pinchuk |
| 5,171,262 A | 12/1992 | MacGregor |
| 5,178,630 A | 1/1993 | Schmitt |
| 5,192,289 A | 3/1993 | Jessen |
| 5,192,307 A | 3/1993 | Wall |
| 5,195,984 A | 3/1993 | Schatz |
| 5,197,977 A | 3/1993 | Hoffman, Jr. et al. |
| 5,197,978 A | 3/1993 | Hess |
| 5,201,757 A | 4/1993 | Heyn |
| 5,209,735 A | 5/1993 | Lazarus |
| 5,211,658 A | 5/1993 | Clouse |
| 5,213,580 A | 5/1993 | Slepian et al. |
| 5,217,483 A | 6/1993 | Tower |
| 5,221,261 A | 6/1993 | Termin et al. |
| 5,226,913 A | 7/1993 | Pinchuk |
| 5,232,446 A | 8/1993 | Arney |
| 5,236,447 A | 8/1993 | Kubo et al. |
| 5,242,451 A | 9/1993 | Harada et al. |
| 5,246,452 A | 9/1993 | Sinnott |
| 5,258,042 A | 11/1993 | Mehta |
| 5,264,276 A | 11/1993 | McGregor et al. |
| 5,271,410 A | 12/1993 | Wolzinger et al. |
| 5,276,276 A | 1/1994 | Gunn |
| 5,282,824 A | 2/1994 | Gianturco |

| | | | | | |
|---|---|---|---|---|---|
| 5,282,846 A | 2/1994 | Schmitt | 5,562,724 A | 10/1996 | Vorwerk et al. |
| 5,282,847 A | 2/1994 | Trescony et al. | 5,562,726 A | 10/1996 | Chuter |
| 5,282,848 A | 2/1994 | Schmitt | 5,562,727 A | 10/1996 | Turk et al. |
| 5,290,305 A | 3/1994 | Inoue | 5,571,166 A | 11/1996 | Dinh et al. |
| 5,306,261 A | 4/1994 | Alliger et al. | 5,571,169 A | 11/1996 | Plaia et al. |
| 5,306,294 A | 4/1994 | Winston et al. | 5,571,172 A | 11/1996 | Chin |
| 5,314,472 A | 5/1994 | Fontaine | 5,571,173 A | 11/1996 | Parodi |
| 5,324,304 A | 6/1994 | Rasmussen | 5,571,176 A | 11/1996 | Taheri |
| 5,324,323 A | 6/1994 | Bui | 5,575,815 A | 11/1996 | Slepian et al. |
| 5,330,528 A | 7/1994 | Lazim | 5,575,816 A | 11/1996 | Rudnick et al. |
| 5,336,254 A | 8/1994 | Brennen et al. | 5,575,817 A | 11/1996 | Martin |
| 5,342,347 A | 8/1994 | Kaplan | 5,578,071 A | 11/1996 | Parodi |
| 5,342,387 A | 8/1994 | Summers | 5,591,197 A | 1/1997 | Orth et al. |
| 5,344,426 A | 9/1994 | Lau et al. | 5,591,198 A | 1/1997 | Boyle et al. |
| 5,348,537 A | 9/1994 | Wiesner et al. | 5,591,228 A | 1/1997 | Edoga |
| 5,354,308 A | 10/1994 | Simon et al. | 5,591,229 A | 1/1997 | Parodi |
| 5,354,309 A | 10/1994 | Schnepp-Pesch et al. | 5,599,305 A | 2/1997 | Hermann et al. |
| 5,356,423 A | 10/1994 | Tihon et al. | 5,607,442 A | 3/1997 | Fischell et al. |
| 5,360,443 A | 11/1994 | Barone et al. | 5,607,444 A | 3/1997 | Lam |
| 5,366,472 A | 11/1994 | Hillstead | 5,607,445 A | 3/1997 | Summers |
| 5,366,473 A | 11/1994 | Winston et al. | 5,609,625 A | 3/1997 | Piplani et al. |
| 5,366,504 A | 11/1994 | Andersen et al. | 5,609,627 A | 3/1997 | Goicoechea et al. |
| 5,370,691 A | 12/1994 | Samson | 5,620,763 A | 4/1997 | House et al. |
| 5,372,600 A | 12/1994 | Beyar | 5,622,188 A | 4/1997 | Plaia et al. |
| 5,382,261 A | 1/1995 | Palmaz | 5,626,561 A | 5/1997 | Butler et al. |
| 5,383,928 A | 1/1995 | Scott et al. | 5,628,783 A | 5/1997 | Quiachon et al. |
| 5,385,580 A | 1/1995 | Schmitt | 5,628,784 A | 5/1997 | Strecker |
| 5,387,235 A | 2/1995 | Chuter | 5,628,788 A | 5/1997 | Pinchuk |
| 5,405,377 A | 4/1995 | Cragg | 5,632,763 A | 5/1997 | Glastra |
| 5,405,378 A | 4/1995 | Strecker | 5,632,772 A | 5/1997 | Alcime et al. |
| 5,413,598 A | 5/1995 | Moreland | 5,637,113 A | 6/1997 | Tartaglia et al. |
| 5,421,955 A | 6/1995 | Lau et al. | 5,639,278 A | 6/1997 | Dereueme et al. |
| 5,423,849 A | 6/1995 | Engelson et al. | 5,643,208 A | 7/1997 | Parodi |
| 5,425,710 A | 6/1995 | Kahir et al. | 5,647,380 A | 7/1997 | Campell et al. |
| 5,425,739 A | 6/1995 | Jessen | 5,649,978 A | 7/1997 | Samson |
| 5,443,500 A | 8/1995 | Sigwart | 5,653,743 A | 8/1997 | Martin |
| 5,449,373 A | 9/1995 | Pinchasik et al. | 5,653,748 A | 8/1997 | Strecker |
| 5,453,084 A | 9/1995 | Moses | 5,662,614 A | 9/1997 | Edoga |
| 5,456,713 A | 10/1995 | Chuter | 5,662,675 A | 9/1997 | Stockert et al. |
| 5,456,721 A | 10/1995 | Legrand | 5,662,701 A | 9/1997 | Plaia et al. |
| 5,458,605 A | 10/1995 | Klemm | 5,662,713 A | 9/1997 | Andersen et al. |
| 5,458,615 A | 10/1995 | Klemm et al. | 5,665,117 A | 9/1997 | Rhodes |
| 5,464,449 A | 11/1995 | Ryan et al. | 5,667,523 A | 9/1997 | Bynon et al. |
| 5,476,506 A | 12/1995 | Lunn | 5,669,924 A | 9/1997 | Shaknovich |
| 5,480,423 A | 1/1996 | Ravenscroft et al. | 5,669,930 A | 9/1997 | Igarashi |
| 5,484,444 A | 1/1996 | Braudschweiler | 5,674,276 A | 10/1997 | Anderson et al. |
| 5,487,858 A | 1/1996 | Schmitt | 5,676,671 A | 10/1997 | Inoue |
| 5,489,295 A | 2/1996 | Piplani et al. | 5,676,696 A | 10/1997 | Marcade |
| 5,496,364 A | 3/1996 | Schmitt | 5,676,697 A | 10/1997 | McDonald |
| 5,496,365 A | 3/1996 | Sgro | 5,681,346 A | 10/1997 | Orth et al. |
| 5,499,994 A | 3/1996 | Tihon et al. | 5,683,449 A | 11/1997 | Marcade |
| 5,507,767 A | 4/1996 | Maeda et al. | 5,683,450 A | 11/1997 | Goicoechea et al. |
| 5,507,769 A | 4/1996 | Marin et al. | 5,683,451 A | 11/1997 | Lenker et al. |
| 5,507,771 A | 4/1996 | Gianturco | 5,683,452 A | 11/1997 | Barone et al. |
| 5,509,902 A | 4/1996 | Raulerson | 5,693,084 A | 12/1997 | Chuter |
| 5,509,931 A | 4/1996 | Schmitt | 5,693,086 A | 12/1997 | Goicoechea et al. |
| 5,514,154 A | 5/1996 | Lau et al. | 5,693,087 A | 12/1997 | Parodi |
| 5,522,822 A | 6/1996 | Phelps et al. | 5,693,088 A | 12/1997 | Lazarus |
| 5,522,880 A | 6/1996 | Barone et al. | 5,695,517 A | 12/1997 | Marin et al. |
| 5,522,881 A | 6/1996 | Lentz | 5,697,970 A | 12/1997 | Schmitt et al. |
| 5,522,961 A | 6/1996 | Leonhardt | 5,700,285 A | 12/1997 | Myers et al. |
| 5,540,701 A | 7/1996 | Sharkey et al. | 5,700,286 A | 12/1997 | Taraglia |
| 5,540,712 A | 7/1996 | Kleshinski et al. | 5,709,657 A | 1/1998 | Zimmon |
| 5,545,210 A | 8/1996 | Hess et al. | 5,713,917 A | 2/1998 | Leonhardt et al. |
| 5,545,211 A | 8/1996 | An et al. | 5,716,365 A | 2/1998 | Goicoechea et al. |
| 5,549,635 A | 8/1996 | Solar | 5,718,724 A | 2/1998 | Goicoechea et al. |
| 5,549,663 A | 8/1996 | Cottone, Jr. | 5,718,973 A | 2/1998 | Lewis et al. |
| 5,554,180 A | 9/1996 | Turk | 5,720,776 A | 2/1998 | Chuter et al. |
| 5,554,181 A | 9/1996 | Das | 5,723,003 A | 3/1998 | Winston et al. |
| 5,554,182 A | 9/1996 | Dinh et al. | 5,723,004 A | 3/1998 | Dereume et al. |
| 5,556,413 A | 9/1996 | Lam | 5,728,131 A | 3/1998 | Frantzen et al. |

| | | |
|---|---|---|
| 5,728,150 A | 3/1998 | McDonald et al. |
| 5,730,698 A | 3/1998 | Fischell et al. |
| 5,732,572 A | 3/1998 | Litton |
| 5,741,274 A | 4/1998 | Lenker et al. |
| 5,741,325 A | 4/1998 | Chaikof et al. |
| 5,749,825 A | 5/1998 | Fischell et al. |
| 5,749,921 A | 5/1998 | Lenker et al. |
| 5,755,769 A | 5/1998 | Richard et al. |
| 5,769,882 A | 6/1998 | Forgarty et al. |
| 5,779,732 A | 7/1998 | Amundson |
| 5,782,904 A | 7/1998 | White et al. |
| 5,800,521 A | 9/1998 | Orth |
| 5,800,522 A | 9/1998 | Campbell et al. |
| 5,800,524 A | 9/1998 | Borghi |
| 5,810,870 A | 9/1998 | Myers et al. |
| 5,824,041 A | 10/1998 | Lenker et al. |
| 5,843,069 A | 12/1998 | Butler et al. |
| 5,843,171 A | 12/1998 | Campbell et al. |
| 5,865,723 A | 2/1999 | Love |
| 5,868,704 A | 2/1999 | Campbell et al. |
| 5,873,906 A | 2/1999 | Lau et al. |
| 5,876,432 A | 3/1999 | Lau et al. |
| 5,888,243 A | 3/1999 | Silvestrini |
| 5,919,225 A | 7/1999 | Lau et al. |
| 5,925,061 A | 7/1999 | Ogi et al. |
| 5,925,075 A | 7/1999 | Myers et al. |
| 5,961,546 A | 10/1999 | Robinson et al. |
| 5,972,441 A | 10/1999 | Campbell et al. |
| 5,976,650 A | 11/1999 | Campbell et al. |
| 5,993,489 A | 11/1999 | Lewis et al. |
| 6,001,123 A | 12/1999 | Lau |
| 6,015,429 A | 1/2000 | Lau et al. |
| 6,015,431 A | 1/2000 | Thornton et al. |
| 6,017,362 A | 1/2000 | Lau |
| 6,019,787 A | 1/2000 | Richard et al. |
| 6,025,044 A | 2/2000 | Campbell et al. |
| 6,027,779 A | 2/2000 | Campbell et al. |
| 6,027,811 A | 2/2000 | Campbell et al. |
| 6,048,484 A | 4/2000 | House et al. |
| 6,086,604 A | 7/2000 | Fischell et al. |
| 6,120,477 A | 9/2000 | Campbell et al. |
| 6,019,788 A | 10/2000 | Butters et al. |
| 6,139,572 A | 10/2000 | Campbell et al. |
| 6,159,565 A | 12/2000 | Campbell et al. |
| 6,165,210 A | 12/2000 | Lau et al. |
| 6,193,745 B1 | 2/2001 | Fogarty et al. |
| 6,203,568 B1 | 3/2001 | Lombardi et al. |

FOREIGN PATENT DOCUMENTS

| | | |
|---|---|---|
| DE | 37 24 514 A1 | 2/1989 |
| DE | 39 18736 A1 | 12/1990 |
| DE | 39 18 736 A1 | 12/1990 |
| DE | 41 37 857 A1 | 5/1992 |
| DE | 197-17-823 A | 11/1997 |
| EP | 0 382 014 | 8/1990 |
| EP | 0 408 245 | 1/1991 |
| EP | 0 418 677 | 3/1991 |
| EP | 0 423 916 B1 | 4/1991 |
| EP | 0 435 518 A1 | 7/1991 |
| EP | 0 464 755 A1 | 1/1992 |
| EP | 0 472 731 | 3/1992 |
| EP | 0 540 290 | 5/1993 |
| EP | 0 551 179 A1 | 7/1993 |
| EP | 0 556 850 | 8/1993 |
| EP | 0 565 251 | 10/1993 |
| EP | 0 667 131 A2 | 1/1995 |
| EP | 0 689 806 A2 | 5/1995 |
| EP | 0 686 379 | 12/1995 |
| EP | 0 696 447 A2 | 2/1996 |
| EP | 0 701 800 A1 | 3/1996 |
| EP | 0 705 577 A1 | 4/1996 |
| EP | 0 716 834 A1 | 6/1996 |
| EP | 0 747 020 A2 | 12/1996 |
| FR | 2 678 508 | 8/1993 |
| GB | 1 506 432 | 4/1978 |
| GB | 1 567 122 | 5/1980 |
| GB | 1 355 373 | 6/1994 |
| JP | 02-174859 | 7/1990 |
| JP | 06-007454 | 1/1994 |
| JP | 06-181993 | 7/1994 |
| JP | 7-500272 T | 1/1995 |
| JP | 07-024688 | 3/1995 |
| JP | 8-509899 T | 10/1996 |
| SU | 1635980 A1 | 12/1988 |
| WO | WO 88/06026 | 8/1988 |
| WO | WO 90/04982 | 5/1990 |
| WO | WO 92/03107 | 3/1992 |
| WO | WO 92/04097 | 3/1992 |
| WO | WO 92/06734 | 4/1992 |
| WO | WO 92/09246 | 6/1992 |
| WO | WO 93/13825 | 7/1993 |
| WO | WO 93/17636 | 9/1993 |
| WO | WO 93/19803 | 10/1993 |
| WO | WO/93/19804 | 10/1993 |
| WO | WO 93/22984 | 11/1993 |
| WO | WO 93/22989 | 11/1993 |
| WO | WO 94/00179 | 1/1994 |
| WO | WO 94/01483 | 1/1994 |
| WO | WO 94/04097 | 3/1994 |
| WO | WO 94/12136 | 6/1994 |
| WO | WO 94/15549 | 7/1994 |
| WO | WO 95/01466 | 2/1995 |
| WO | WO 95/05131 | 2/1995 |
| WO | WO 95/05132 | 2/1995 |
| WO | WO 95/09586 | 4/1995 |
| WO | WO 95/21592 | 8/1995 |
| WO | WO 95/26695 | 10/1995 |
| WO | WO 96/10967 | 4/1996 |
| WO | WO 96/18360 | 6/1996 |
| WO | WO 96/18361 | 6/1996 |
| WO | WO 96/24306 | 8/1996 |
| WO | WO 97/21402 | 6/1997 |
| WO | WO 97/21403 | 6/1997 |
| WO | WO 97/21641 | 6/1997 |
| WO | WO 98/30173 | 7/1998 |

OTHER PUBLICATIONS

Cragg, et al; *Nitinol Intravascular Stent: Results of Preclinical Evaluation;* Radiology; pp. 775–778; Dec. 1993; vol. 189, No. 3.

Cragg, "Percutaneous Femoropopliteal Graft Placement" *Radiology* (1993) 187 (3): 643–648.

Hagen et al, "Self–Expandable Macroporous Nitinol Stents for Transfemoral Exclusion of Aortic Aneurysms in Dogs: Preliminary Results" *Cardiovascular Intervention Radiology* (1993) 16:339–342.

Laborde et al., "Intraluminal Bypass of Abdominal Aortic Aneurysm: Feasibility Study"; *Radiology* 1992, 184: 185–190.

Product Brochure for Cook–Z Stents, Gianturco–Rösch Biliary Design, Cook®, a Cook Groups Company, P.O. box 489, Bloomington, IN, 47402, U.S.A., 4 pgs. total, (1989).

Neuwirth, MinTec™ Minimally Invasive Technologies Product Brochure for the Craggstent and Cragg EndoPro System 1, 4 pgs.

Blum, U. et al.; "Dacron Endografts for Infrarenal Abdominal Aortic Aneurysms: 2 Year Follow–up"; Fifth international and Interdisciplinary Symposium on Endoluminal Stents and Grafts (Oct. 10–13, 1996) Washington, D.C., 2 pages total.

Chuter et al.; "Bifurcated stent–grafts for AAA: 3 year follow–up"; Abstracts from the Seventh International Course on Peripheral Vascular Intervention; J. Endovas. Surg. (1996) 3:453.

Chuter et al.; "Bifurcated stent–grafts for AAA: 3 year follow–up", *Fifth International and Interdisciplinary Symposium on Endoluminal Stents and Grafts* (Oct. 10–13, 1996) Washington, D.C., 2 pages total.

Dereume, JP et al.; "Endoluminal Treatment of Abdominal Aortic Aneurysm with the Corvita Endovascular Graft, Results of a Single–Center, Prospective Feasibility Study of 90 Patients"; *Abstracts from the Seventh International Course on Peripheral Vascular Intervention* J. Endovasc. Surg. (1996) 3:460–461.

Katzen et al.; "Initial experience performing conbined surgical/intervention procedures in the interventional suite" *Abstracts from the Seventh International Course on Peripheral Vascular Intervention J. Endovasc. Surg.* (1996) 3:467.

Moore et al., "Transfermoral endovascular repair of abdominal aortic aneurysm: Result of the North American EVT phase 1 trial" J. Vasc. Surg. (1996) 23:543–552.

Parodi et al., "long–term follow–up of AAA endoluminal repair" Abstracts from the Seventh International Course on Peripheral Vascular Intervention. J. Endovasc. Surg. (1996) 3:335.

White et al., "Endoleak following endoluminal repair of AAA: Diagnosis, significance, and amanagement" *Abstracts from the Seventh International Course on Peripheral Vascular Intervention J. Endovasc. Surg.* (1996) 3:339–340.

Wilson et al.; "A self expanding bifurcated endovascular graft for Abdominal Aortic Aneurysm Repair. An Initial Study in a Canine Model" ASAIO Journal 42(5): 386–393 (1996).

World Medical News, World Medical manufacturing Corporation, 13794 NW 4th Street, Bldgs. 210 & 211, Sunrise, Florida, 33325 U.S.A., vol. 5, Issue 3 (Jul. 1996) 3 pages total.

U.S. application No. 08/871,427, Lau, et al., filed Jun. 9, 1997 and pending claims as of Apr. 16, 2001.

U.S. application No. 09/207,944, Vonesh et al., filed Dec. 9, 1998 and response dated Aug. 21, 2000.

U.S. application No. 09/235,214, Brauker et al., filed Jan. 22, 1999.

U.S. application No. 09/235,458, Vonesh et al., filed Jan. 22, 1999 and response dated Sep. 28, 2000.

U.S. application No. 09/306,522, Myers, filed May 6, 1999.

U.S. application No. 09/408,866, Brenton et al., filed Sep. 30, 1999 and response dated Jan. 10, 2001.

U.S. application No. 09/488,229, Cully et al., filed Jan. 20, 2000.

U.S. application No. 09/489,604, Vonesh et al., filed Jan. 20, 2000.

U.S. application No. 09/510,937, Goffena et al., filed Feb. 22, 2000 and response dated Oct. 5, 2000.

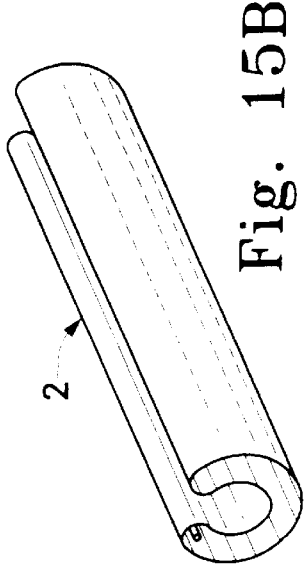
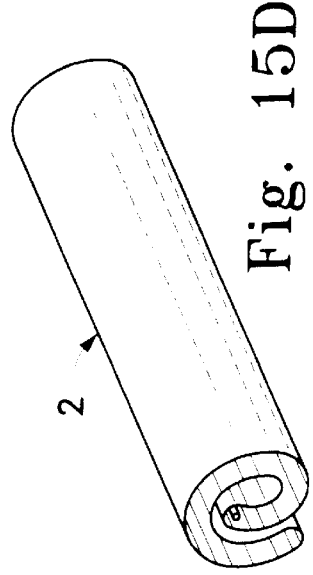
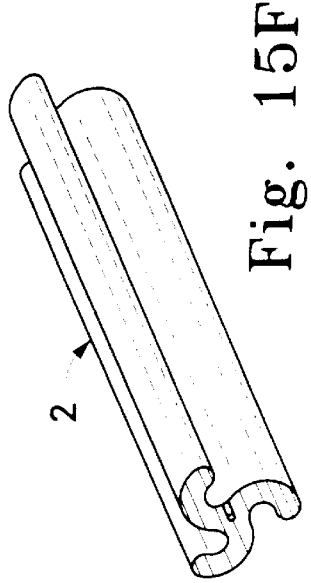
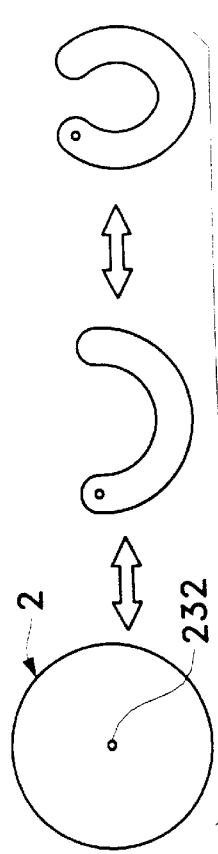
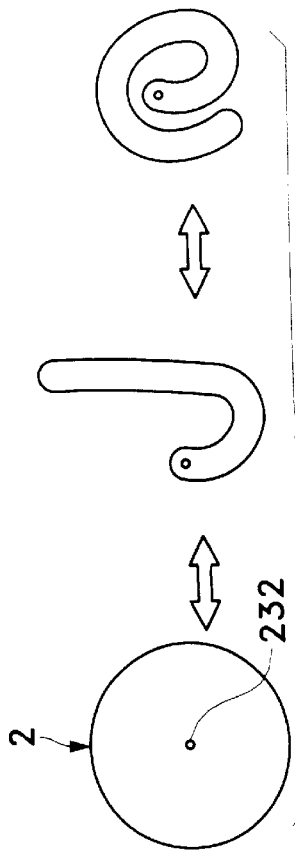
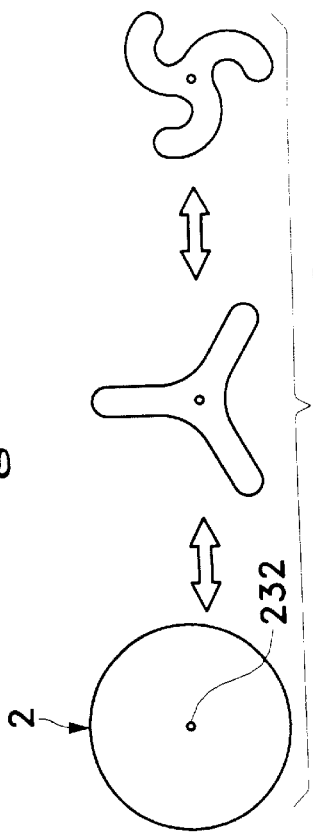

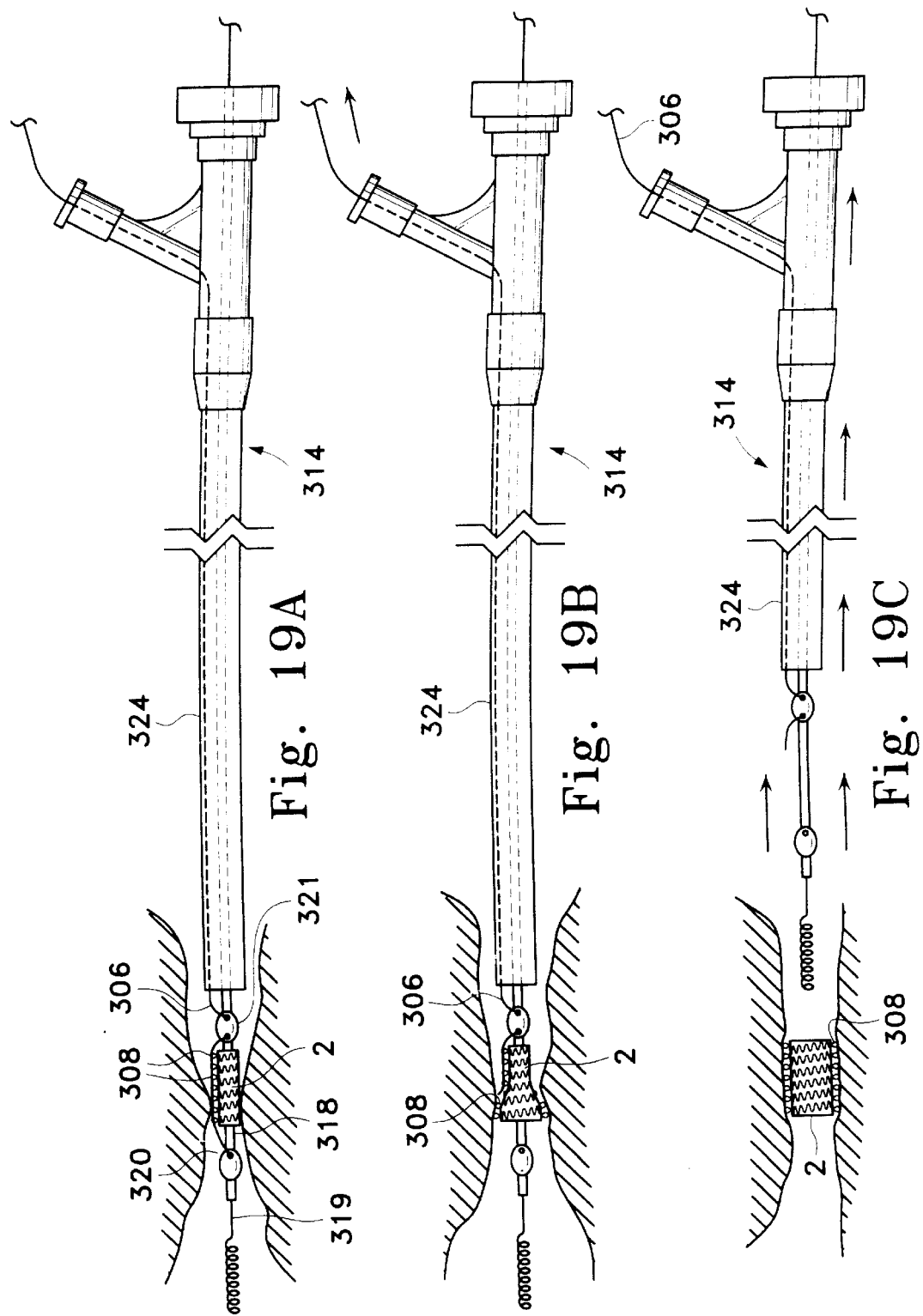

METHOD OF MAKING A KINK RESISTANT STENT-GRAFT

CONTINUING DATA

This application is a divisional application of U.S. application Ser. No. 08/896,805, filed Jul. 18, 1997, now U.S. Pat. No. 6,042,605, which is a continuation-in-part of Ser. No. 08/572,548, filed Dec. 14, 1995, now abandoned, the entirety of which is incorporated herein by reference.

FIELD OF THE INVENTION

This invention relates generally to implants for repairing ducts and passageways in the body. More specifically, the invention relates to an expandable stent-graft.

BACKGROUND OF THE INVENTION

Treatment or isolation of vascular aneurysms or of vessel walls which have been thinned or thickened by disease has traditionally been performed via surgical bypassing with vascular grafts. Shortcomings of this procedure include the morbidity and mortality associated with surgery, long recovery times after surgery, and the high incidence of repeat intervention needed due to limitations of the graft or of the procedure.

Vessels thickened by disease are currently sometimes treated less invasively with intraluminal stents that mechanically hold these vessels open either subsequent to or as an adjunct to a balloon angioplasty procedure. Shortcomings of current stents include the use of highly thrombogenic materials (stainless steels, tantalum, ELGILOY) which are exposed to blood, the general failure of these materials to attract and support functional endothelium, the irregular stent/vessel surface that causes unnatural blood flow patterns, and the mismatch of mechanical compliance and flexibility between the vessel and the stent.

Various attempts have been made to provide a nonthrombogenic blood-carrying conduit. Pinchuk, in U.S. Pat. Nos. 5,019,090, 5,092,887, and 5,163,958, suggests a spring stent which appears to circumferentially and helically wind about as it is finally deployed except, perhaps, at the very end link of the stent. The Pinchuk '958 patent further suggests the use of a pyrolytic carbon layer on the surface of the stent to present a porous surface of improved antithrombogenic properties.

U.S. Pat. No. 5,123,917, to Lee, suggests an expandable vascular graft having a flexible cylindrical inner tubing and a number of "scaffold members" which are expandable, ring-like and provide circumferential rigidity to the graft. The scaffold members are deployed by deforming them beyond their plastic limit using, e.g., an angioplasty balloon.

A variety of stent-graft designs also have been developed to improve upon simple stent configurations. Perhaps the most widely known stent-graft is shown in Ersek, U.S. Pat. No. 3,657,744. Ersek shows a system for deploying expandable, plastically deformable stents of metal mesh having an attached graft through the use of an expansion tool.

Palmaz describes a variety of expandable intraluminal vascular grafts in a sequence of patents: U.S. Pat. Nos. 4,733,665; 4,739,762; 4,776,337; and 5,102,417. The Palmaz '665 patent suggests grafts (which also function as stents) that are expanded using angioplasty balloons. The grafts are variously a wire mesh tube or of a plurality of thin bars fixedly secured to each other. The devices are installed, e.g., using an angioplasty balloon and consequently are not seen to be self-expanding. The Palmaz '762 and '337 patents appear to suggest the use of thin-walled, biologically inert materials on the outer periphery of the earlier-described stents. Finally, the Palmaz '417 patent describes the use of multiple stent sections each flexibly connected to its neighbor.

Rhodes, U.S. Pat No. 5,122,154, shows an expandable stent-graft made to be expanded using a balloon catheter. The stent is a sequence of ring-like members formed of links spaced apart along the graft. The graft is a sleeve of a material such as an expanded polyfluorocarbon, expanded polytetrafluoroethylene available from W. L. Gore & Associates, Inc. or IMPRA Corporation.

Schatz, U.S. Pat. No. 5,195,984, shows an expandable intraluminal stent and graft related in concept to the Palmaz patents discussed above. Schatz discusses, in addition, the use of flexibly-connecting vascular grafts which contain several of the Palmaz stent rings to allow flexibility of the overall structure in following curving body lumen.

Cragg, "Percutaneous Femoropopliteal Graft Placement", *Radiology,* vol. 187, no. 3, pp. 643–648 (1993), shows a stent-graft of a self-expanding, nitinol, zig-zag, helically wound stent having a section of polytetrafluoroethylene tubing sewed to the interior of the stent.

Cragg (European Patent Application 0,556,850) discloses an intraluminal stent made up of a continuous helix of zig-zag wire and having loops at each apex of the zig-zags. Those loops on the adjacent apexes are individually tied together to form diamond-shaped openings among the wires. The stent may be made of a metal such as nitinol (col. 3 lines 15–25 and col. 4, lines 42+), and may be associated with a "polytetrafluoroethylene (PTFE), dacron, or any other suitable biocompatible material". Those biocompatible materials may be inside the stent (col. 3 lines 52+) or outside the stent (col. 4, lines 6+).

WO93/13825 to Maeda et al. discloses a self-expanding stent having a wire bent into an elongated zig-zag pattern and helically would about a tubular shape interconnected with a filament. A sleeve may be attached to the outer or inner surface of the stent.

PCT application publication WO/95/05132 discloses a stent-graft with a tubular diametrically adjustable stent.

There is a need for an alternate stent-graft construction that exhibits excellent kink resistance and flexibility.

SUMMARY OF THE INVENTION

The present invention involves a stent-graft including a stent member having an inner surface and an outer surface, a generally tubular graft member and a coupling member that couples the stent member to the graft member. The coupling member, which in the preferred embodiment is in the form of a ribbon, covers only a portion of at least one of the inner or outer surface of the stent member and secures the stent member and graft member to one another. Alternatively, the coupling member can be described as interconnecting less than entirely the inner or outer surface of the stent member to the graft member.

With this construction, regions of the stent member do not interface with the coupling member. This is believed to advantageously reduce shear stresses between the stent member and the coupling member when the stent-graft undergoes bending so that tearing of the coupling and/or graft member can be minimized or eliminated. It is also believed that this arrangement minimizes the likelihood of delamination between the coupling member and the graft. If_ delamination were to occur, the inner portion of the stent-graft could perceivable collapse into the vessel lumen and interfere with desired blood flow. Thus, the stent-graft is believed to be capable of conforming to curves in a blood vessel lumen with minimal risk of tearing the graft or coupling member, or delamination between the stent and graft members.

According to another aspect of the invention, the coupling member is secured to the graft member without sutures. When the graft member is placed within the stent member, for example, this arrangement eliminates the need for having sutures extend into the lumen formed by the graft member and possibly interfere with blood flow. Another benefit of this arrangement, as compared to suturing the stent to the graft member, is that suture holes need not be placed in the graft which could adversely affect its integrity. The coupling member may be thermally or adhesively bonded to the graft member.

The coupling member preferably has a generally broad or flat working surface as compared to filament or thread-like structures such as sutures. As noted above, a preferred coupling member is in the form of a ribbon. This configuration advantageously increases potential bonding surface area between the coupling member and the graft member to enhance the integrity of the bond therebetween. The increased bonding surface may facilitate minimizing the thickness of the coupling member so that the stent-graft lumen volume and blood flow dynamics therein can be optimized. For example, a thicker coupling member would increase the overall stent-graft thickness which can cause an undesirable lumen diameter reduction at the transition where the vessel lumen interfaces the inlet of the stent-graft. This, in turn, can result in undesirable turbulent flow which possibly can lead to complications such as thrombosis.

According to a preferred embodiment of the invention, the coupling member is arranged in a helical configuration with multiple turns. Each of a number of the coupling member turns is spaced from the turn(s) adjacent thereto. With this construction, a generally uniform distribution of coupling member-free stress relief zones may be achieved. Elastic wrinkling in the graft member may occur in those zones so that the graft member can absorb stress when bent along its longitudinal axis, for example, and resist kinking.

According to a preferred stent member construction for use with the stent-graft of the present invention, at least a portion of the stent member includes undulations and is arranged in a helical configuration with multiple turns. Each stent member undulation includes an apex and an open base portion. The apexes and base portions are configured so as not to restrain one apex into the undulation in an adjacent turn and substantially in-phase therewith when the stent-graft is bent or compressed. This is believed to facilitate undulation movement during bending or compression and minimize the likelihood of stress build-up that may cause kinking. The coupling member typically covers a substantial portion of each undulation so as to minimize the likelihood of the stent member apexes bending away from the graft member and interfering with the environment or tether line which may be used to maintain the stent-graft in a folded state before deployment. The coupling member also may be positioned adjacent to the apexes to minimize the likelihood of such apex movement.

According to another aspect of the invention, the end portions of the stent-member also may be enveloped between the coupling member or discrete coupling members and the graft member. This prevents the terminal portions of the stent and graft members from significantly moving away from one another. For example, when the stent-member is external to the graft member, the terminal graft portions may flap away from the stent member and possibly interfere with blood flow if the terminal coupling portions were not present.

According to another feature of the invention, the stent-graft is advantageously manufactured by placing a cushioning layer around a mandrel, assembling the stent-graft on the cushioning layer, surrounding the mandrel mounted assembly with a multi-component member formed from a PTFE tube having a longitudinal slit and which is wrapped with an expanded PTFE or other film or tape to compress the assembly, and heating the assembly to bond a coupling member to the graft.

The above is a brief description of some deficiencies in the prior art, and advantages and aspects of the present invention. Other features, advantages, and embodiments of the invention will be apparent to those skilled in the art from the following description, accompanying drawings and appended claims.

BRIEF DESCRIPTION OF THE DRAWINGS

FIGS. 15A, 15C and 15E show procedures for folding the stent-grafts. FIGS. 15B, 15D, and 15F show the corresponding folded stent-grafts.

FIGS. 19A, 19B, and 19C diagrammatically show a procedure for deploying the stent-grafts shown in FIGS. 17A–17C and 18A–18C using a tether wire.

DESCRIPTION OF THE PREFERRED EMBODIMENTS

Figure 1A:
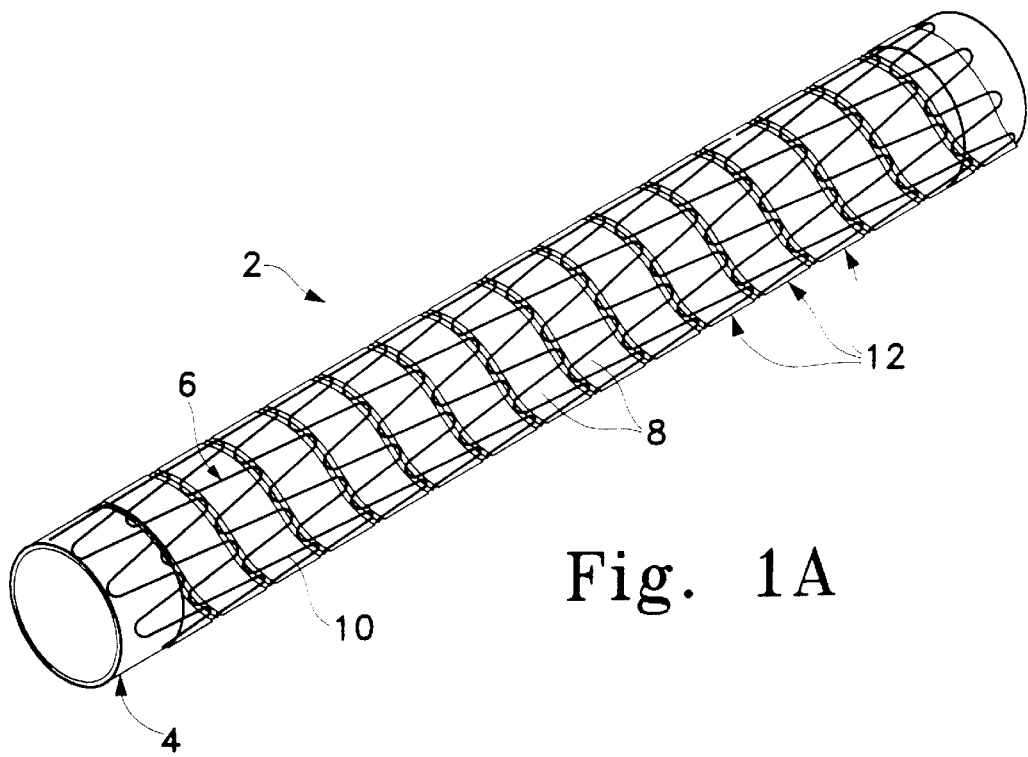
FIG. 1A is a perspective view of a stent-graft constructed in accordance with the principles of the present: invention.

Referring to the drawings in detail wherein like numbers indicate like elements, an expandable stent-graft 2 is shown constructed according to the principles of the present invention. Although particular stent and graft constructions will be described in conjunction with the preferred embodiments, it should be understood that other constructions may be used without departing from the scope of the invention.

Referring to FIGS. 1A and B, stent-graft 2 generally includes a thin-walled tube or graft member 4, a stent member 6 and a coupling member 8 for coupling the stent and graft members together. Preferably, the stent and graft members are coupled together so that they are generally coaxial.

Figure 1B:
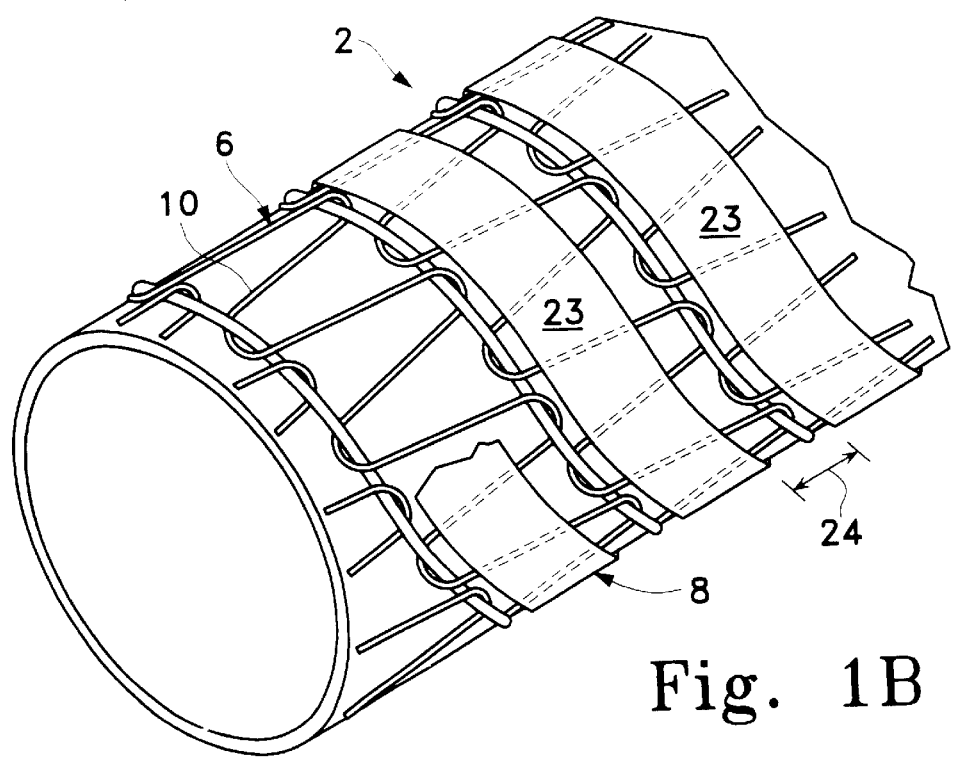
FIG. 1B is an enlarged perspective view of a mid-portion of the stent-graft shown in FIG. 1A.

Tubular expandable stent member 6 is generally cylindrical and comprises a helically arranged undulating member 10 having plurality of helical turns 12 and preferably comprising nitinol wire. The undulations preferably are aligned so that they are "in-phase" with each other as shown in FIGS. 1A and 1B, for example. More specifically, undulating helical member 10 forms a plurality of undulations 14, each including an apex portion 16 and a base portion 18. When the undulations are in-phase, apex portions 16 in adjacent helical turns 12 are aligned so that an apex portion 16 may be displaced into a respective base portion 18 of a corresponding undulation in-phase therewith and in an adjacent helical turn.

Once the undulations are aligned so that adjacent undulations in one turn are in-phase with the undulations in the helical turns adjacent thereto, a linking member 20 may be provided to maintain the phased relationship of the undulations during compression and deployment, and during bending of the stent member. In the illustrative embodiment, linking member 20 is laced or interwoven between undulations in adjacent turns of the helical member and acquires a helical configuration (See, e.g., FIGS. 1–3). Linking member 20 preferably comprises a biocompatible polymeric or metallic material having sufficient flexibility to be readily folded upon itself.

Undulations 14 preferably are unconfined in that they are configured so as not to tend to inhibit the movement of flexible link 20 down between respective torsion arms or lengths 22a and 22b. In addition, the undulations preferably are configured and arranged so that a respective apex portion can readily move within a corresponding undulation base portion 18 in-phase therewith. It is believed that this construction minimizes the likelihood of stress build-up, for example, during bending or compression (as depicted in the lower portion of FIG. 6) and, thus, improves the kink resistance of the stent-graft.

Figure 3A:
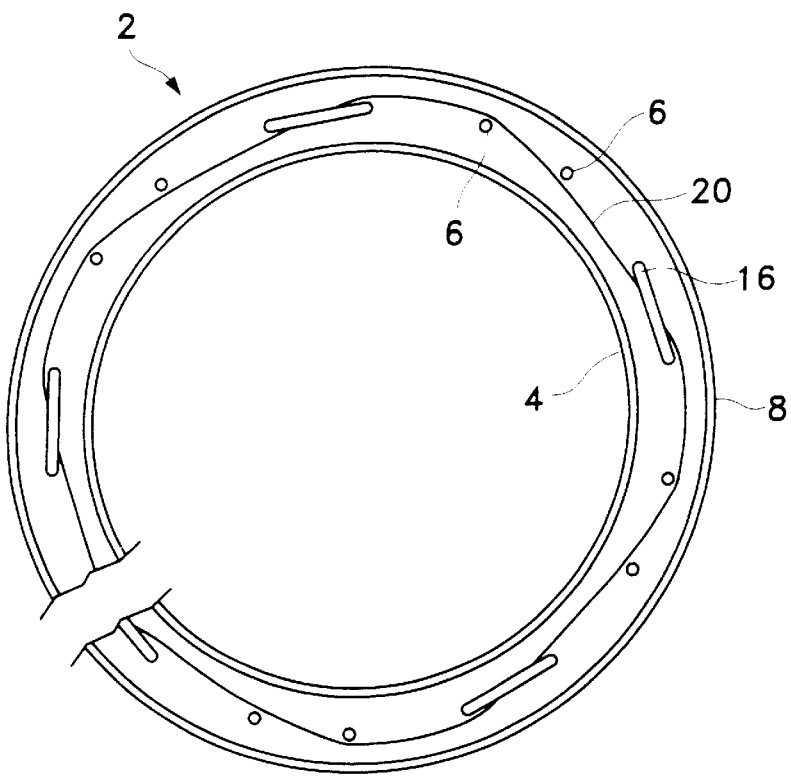
FIG. 3A is a diagrammatic representation of a transverse section of the stent-graft of FIG. 1 prior to the coupling and graft members being secured to one another.
Figure 3B:
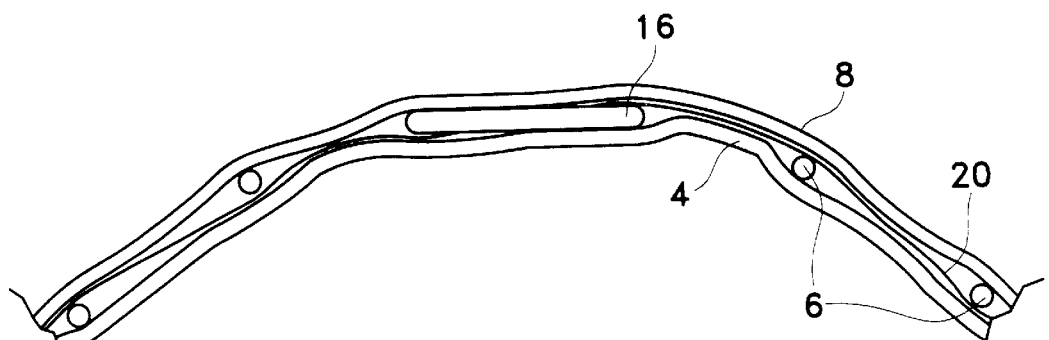
FIG. 3B is an enlarged portion of the section shown in FIG. 3A after the coupling and graft members have been secured to one another.

Referring to FIGS. 3A and 3B, stent member 6 is disposed between generally tubular graft member 4 and coupling member 8. The stent member provides a support structure for the graft member to minimize the likelihood of the graft member collapsing during use. Although the graft member may surround the outer surface of the stent member, it preferably is placed within the stent member to provide a relatively smooth (wrinkles may form in the graft member between coupling member turns during compression) intralumental stent-graft surface as shown in the drawings.

An important aspect of the invention is that the coupling member, which secures the stent member to the graft member, covers only a portion of the stent member. Alternatively, the coupling member can be described as is preferably interconnecting less than entirely the inner or outer surface of the stent member to the graft member (e.g., it covers less than all of the outer surface of the stent member when the graft member is positioned inside the stent member). With this construction, regions of the stent member do not interface with the coupling member when the stent-graft is an uncompressed state, for example. This is believed to advantageously reduce shear stresses between the stent member and the coupling member when the stent-graft undergoes bending or compression, thereby reducing the risk of tearing the graft or coupling member or causing delamination between the stent and graft members.

The coupling member also preferably has a generally broad or flat surface for interfacing with the stent and graft members as compared to filament or thread-like structures such as sutures. This increases potential bonding surface area between the coupling member and the graft member to enhance the structural integrity of the stent-graph. The increased bonding surface area also facilitates minimizing the thickness of the coupling member. It has been found that a coupling member in a form of a generally flat ribbon or tape as shown in the drawings and designated with reference numeral 8, provides the desired results.

Figure 2:
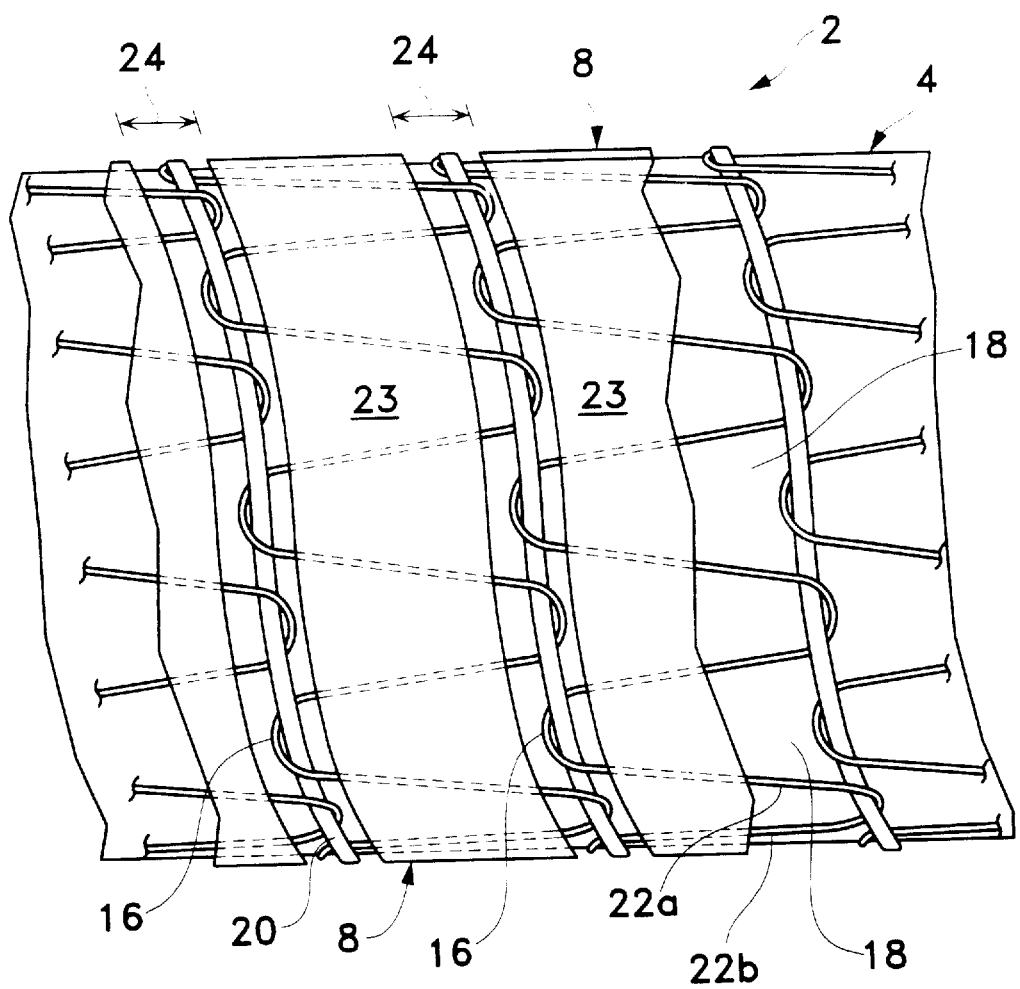
FIG. 2 is a side view of an enlarged portion of the stent-graft shown in FIG. 1A.

As noted above, coupling member 8 preferably is in the form of a generally flat ribbon or tape having at least one generally flat surface. In addition, coupling member 8 is arranged in a helical configuration according to the preferred embodiments illustrated in the drawings. Referring to FIG. 2, helically arranged coupling member 8 is formed with multiple helical turns 23, each being spaced from the turns adjacent thereto, thereby forming coupling member-free stress relief zones 24 between adjacent turns. The coupling member also preferably is arranged to provide a generally uniform distribution of stress relief zones 24. In the illustrated embodiments, coupling member 8 is helically wound around the stent member with its helical turns 23 aligned with the stent member turns 12. As shown, the coupling member may be constructed with a constant width and arranged with uniform spacing between turns.

Coupling member 8 also preferably covers a substantial portion of each undulation so as to minimize the likelihood of the stent member apexes lifting away from the graft member and interfering with their immediate environment.

Coupling members having widths of 0.025, 0.050 and 0.075 inches have been applied to the illustrated stent member having a peak-to-peak undulation amplitude of about 0.075 inch with suitable results. However, it has been found that as the coupling member band width increases, the stent-graft flexibility generally is diminished. It is believed that coupling member width of about one-forth to three-fourths the amplitude of undulations 14, measured peak-to-peak, is preferred (more preferably about one third to two thirds that amplitude) to optimize flexibility. It also has been found that by positioning one of lateral margins of the ribbon-shaped coupling member 8 adjacent to the apexes, e.g., in abutment with linking member 20, the coupling member width may be reduced without significantly sacrificing apex securement. Varying the width of the coupling member can also result in the adjustment of other structural properties. Increasing the width can also potentially increase the radial stiffness and the burst pressure and decrease the porosity of the device. Increasing band width can also diminish graft member wrinkling between coupling member turns.

Figure 11:
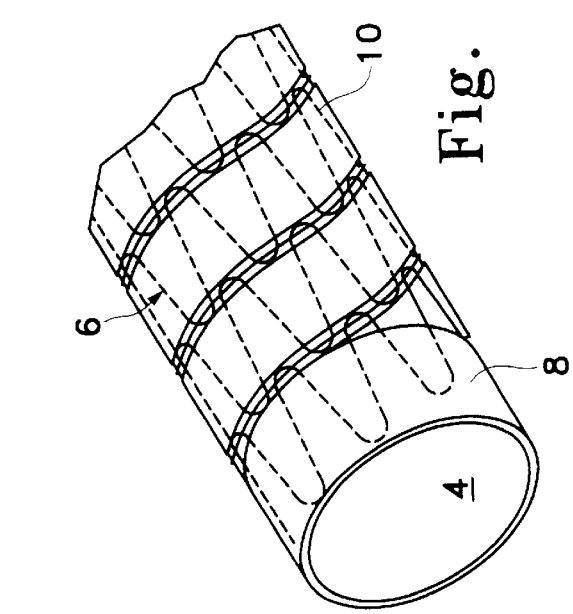
FIG. 11 is a partial view of the stent-graft of FIG. 1A showing an end portion of the device.

Coupling member 8 (or separate pieces thereof) also surrounds the terminal end portions of the stent-graft to secure the terminal portions of the graft member to the support structure formed by stent member 6 as shown in FIG. 11, for example.

Figure 4:
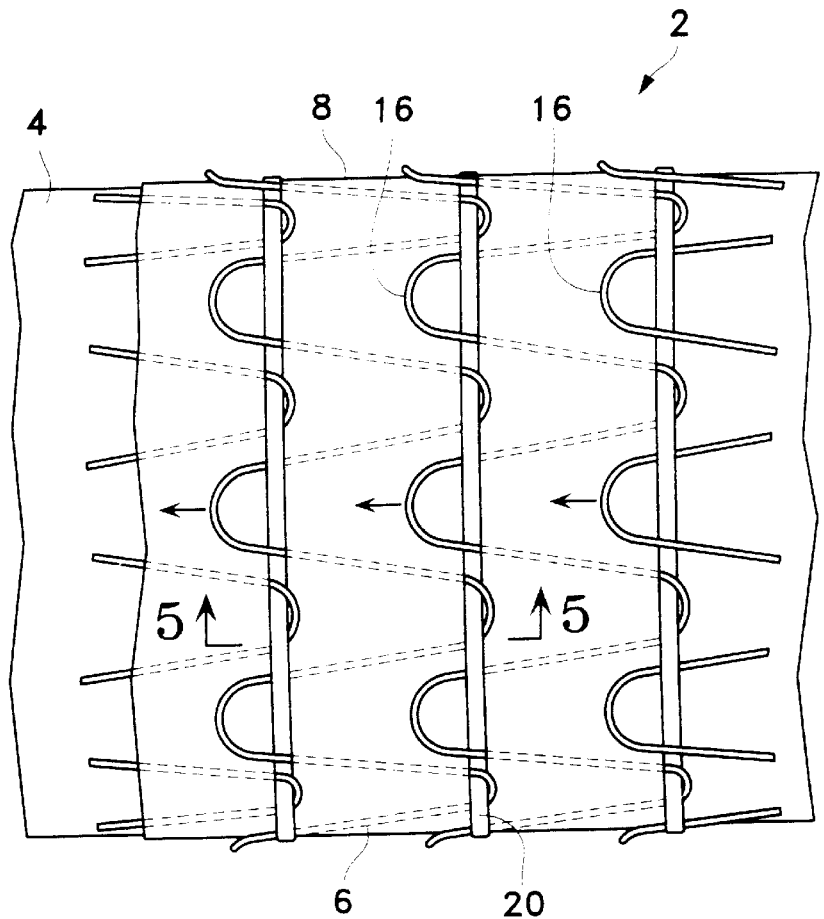
FIG. 4 illustrates the stent-graft of FIGS. 1A & 1B under longitudinal, axial compression.
Figure 5:
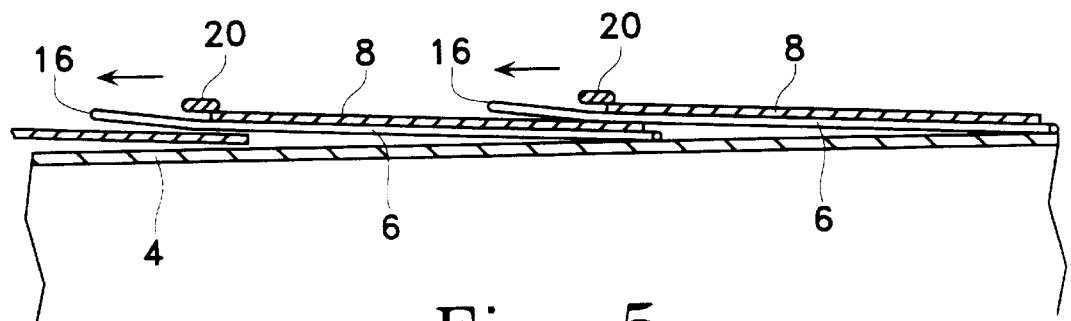
FIG. 5 is a sectional view of the stent-graft of FIGS. 1A and 1B taken along line 5—5 in FIG. 4.
Figure 6:
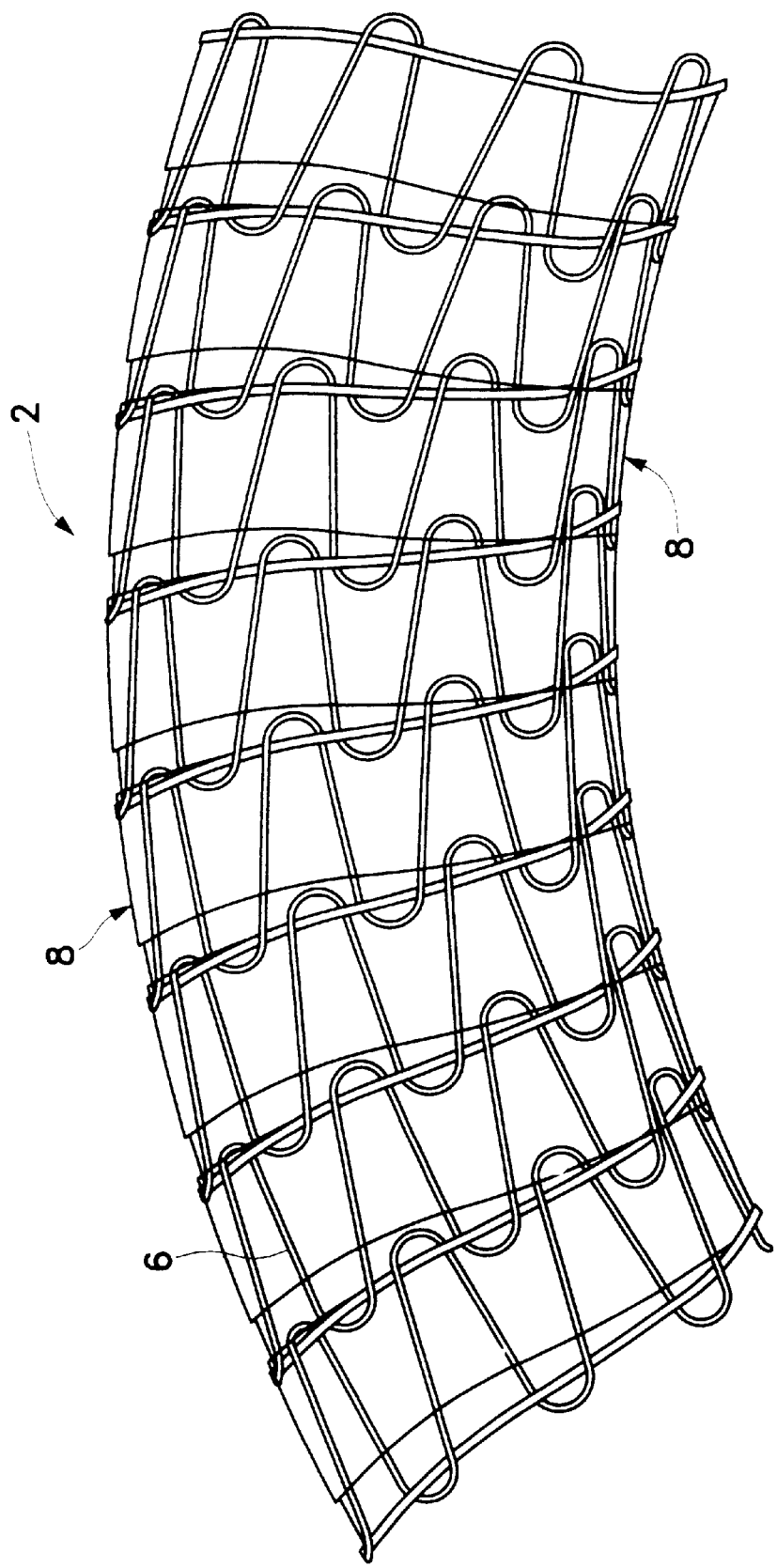
FIG. 6 diagrammatically shows a portion of the stent-graft of FIGS. 1A and 1B bent along its longitudinal axis.
Figure 7:
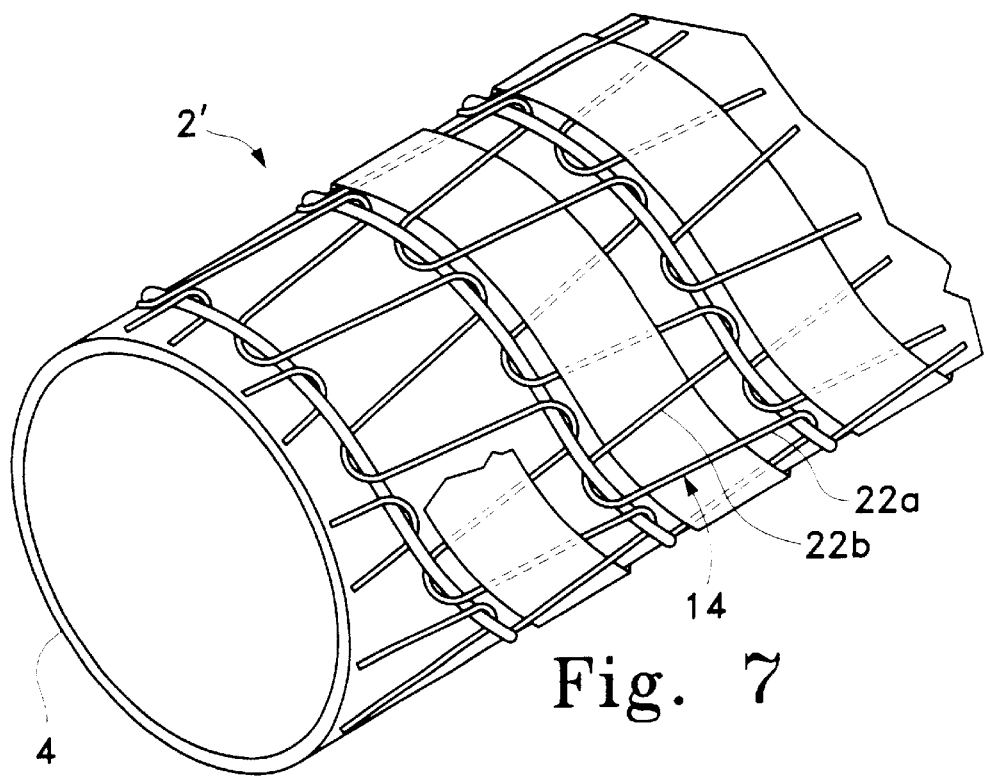
FIG. 7 is a perspective view of another embodiment of the stent-graft of the present invention having an alternate stent to graft coupling configuration.
Figure 8:
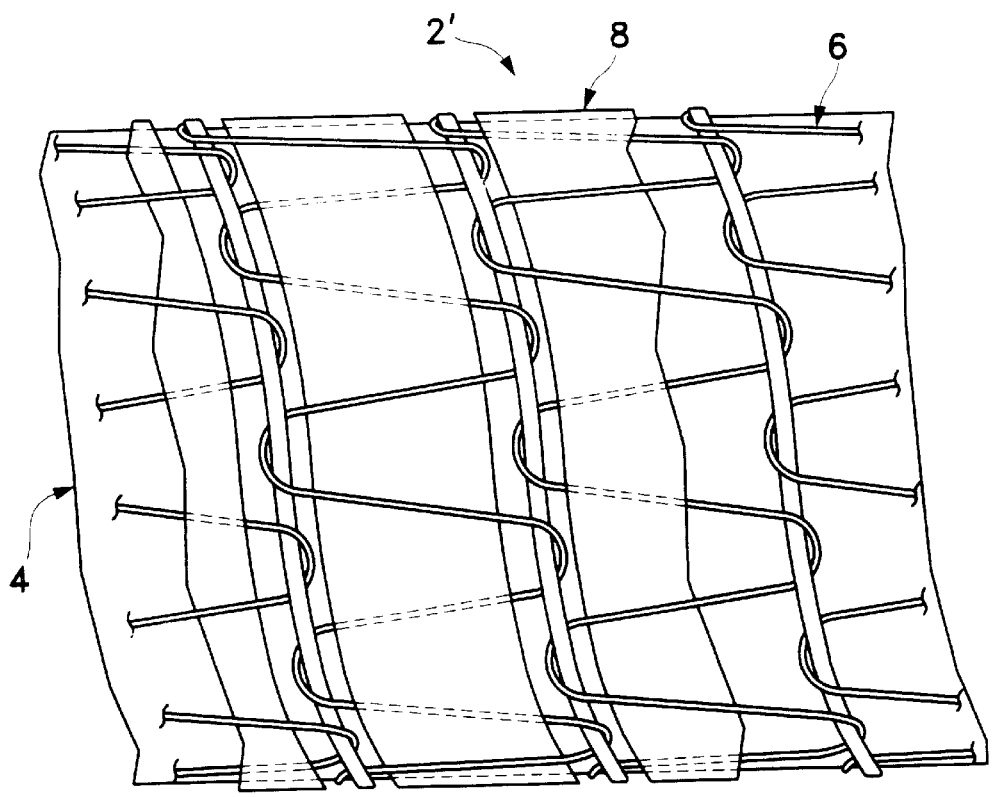
FIG. 8 is a side view of an enlarged portion of the stent-graft shown in FIG. 7.
Figure 9:
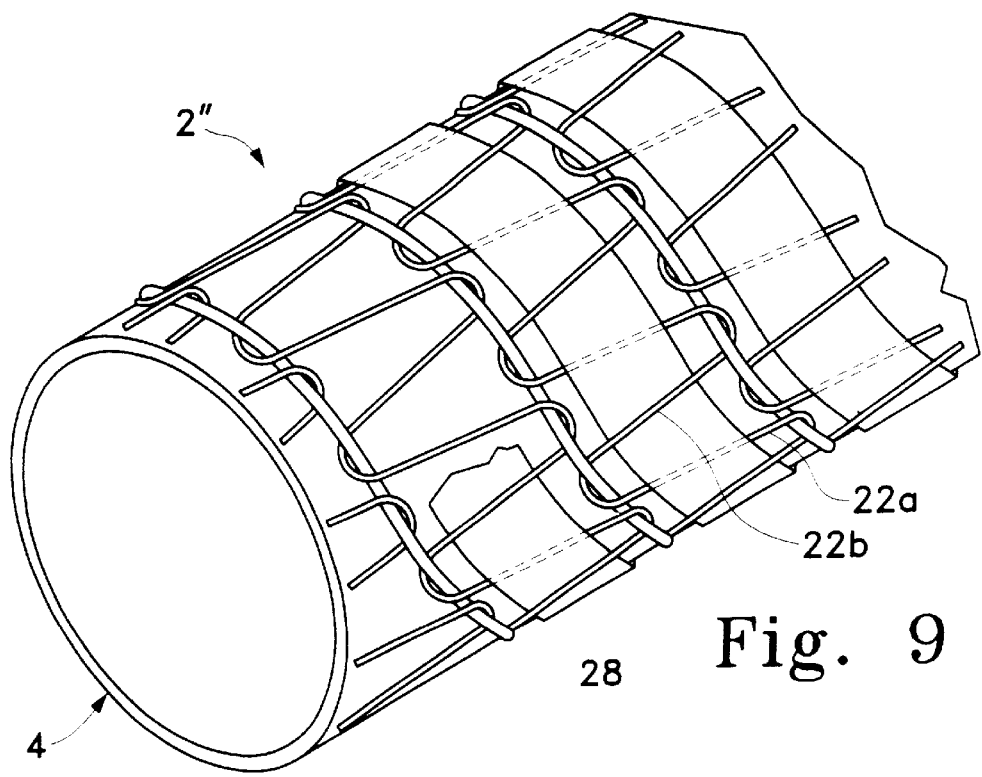
FIG. 9 is a perspective view of a further embodiment of the stent-graft of the present invention having yet another stent to graft coupling.
Figure 10:
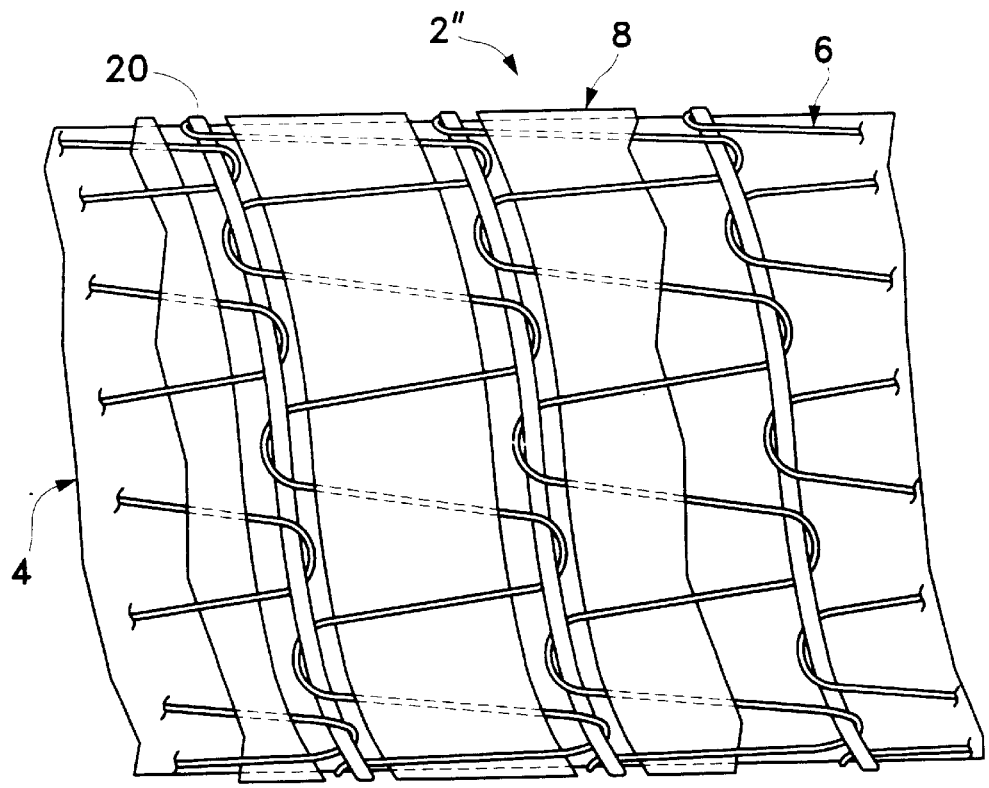
FIG. 10 is a side view of an enlarged portion of the stent-graft shown in FIG. 9.

Although the coupling member may cover a substantial portion of each undulation as discussed above, apex portions 16 may still move within the undulations in-phase therewith as shown in FIGS. 4–6 due primarily to the flexibility of coupling and linking members 8 and 20 respectively. Further, coupling member 8 may be wrapped so as to be completely external to stent member 6 as shown in FIGS. 1–6, interwoven above and below alternating undulations 14 as shown in FIGS. 7 and 8, or interwoven above and below alternating undulation arms 22a and 22b as shown in FIGS. 9 and 10. In addition, the ribbon-shaped tape or coupling member 8 may be axially spaced away from the apexes and linking member 20 (FIGS. 9 and 10) as compared to the embodiments shown in FIGS. 1–8. This spacing provides an area 28 in which linking member 20 can freely move without restraint, thereby reducing any resistance placed on apexes moving into corresponding undulations during compression or bending.

The coupling member 8 may be wrapped (placed) on or interwoven with the undulations of the stent before or after it is positioned around the graft. For example the coupling member may be placed on or interwoven with the undulations of element 10 of FIG. 14A. As a result of fluorinated ethylene propylene (FEP) coating on a surface of the coupling member, element 10 will be bonded to the coupling member by heating. The resulting element is then configured into the stent of this invention. Placing or wrapping the coupling member is performed in a manner similar to that described and shown for FIGS. 1–11.

Although a particular coupling member configuration and pattern has been illustrated and described, other configuration and/or patterns may be used without departing from the scope of the present invention. For example, coupling member(s) arranged in a multiple helix (e.g., a double or triple helix) may be used. Longitudinally extending strips of ribbon may be used and may be preferred when the coupling member is used in conjunction with other stent member configurations.

Figure 12:
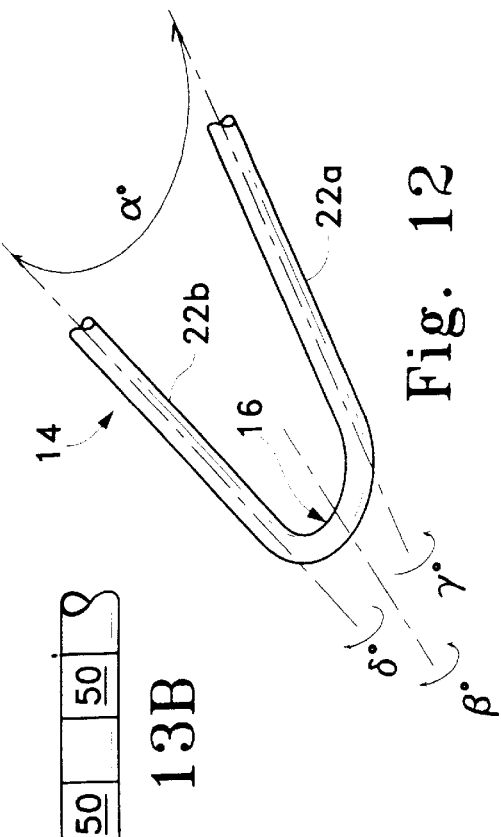
FIG. 12 is an abstracted portion of a suitable stent and shows the concept of torsion on a portion of that stent.

Each undulation 14 alternatively may be described as a torsion segment and for purposes of the following discussion will be referred to as a torsion segment 14. Referring to FIG. 12, an isolated undulation 14 is shown to facilitate the following discussion involving stent mechanics involved in deployment of the device. Each torsion segment includes an apex portion 16 and two adjacent torsion arms or lengths 22a and 22b extending therefrom. Typically, then, each torsion arm 22a & b will be a component of each of two adjacent torsion segments 14. When torsion segment 14 undergoes a flexing in the amount of $\alpha$ apex portion 16 will flex some amount $\beta°$, torsion arm 22a will undertake a twist of $\gamma°$ and torsion arm 22b will undertake a twist opposite of that found in torsion arm 22a in the amount of $\delta°$. The amounts of angular torsion found in the torsion arms (22a & 22b) will not necessarily be equal because the torsion arms will not necessarily be equal because the torsion arms are not necessarily at the same angle to the longitudinal axis of the stent-member. Nevertheless, the sum of $\beta°+\gamma°+\delta°$ will equal $\alpha°$. When a value of $\alpha°$ is chosen, as by selection of the shape and size of the stent-member upon folding, the values of the other three angles ($\beta°$, $\gamma°$, $\delta°$) are chosen by virtue of selection of number or torsion segments around the stent, size and physical characteristics of the wire, and length of the torsion areas (22a & b). Each of the noted angles must not be so large as to exceed the values at which the chosen material of construction plastically deforms at the chosen value of $\alpha°$.

To further explain: it should be understood that torsion segment 14 undergoes a significant amount of flexing as the stent-member is folded or compressed in some fashion. The flexing provides a twist to the torsion arms (22a & b), a significant portion of which is generally parallel to the longitudinal axis of the stent.

The described stent-member uses concepts which can be thought of as widely distributing and storing the force necessary to fold the tubular stent into a configuration which will fit through a diameter smaller than its relaxed outside diameter without inducing plastic deformation of the constituent metal or plastic and yet allowing those distributed forces to expand the stent upon deployment.

Once the concept of distributing the folding or compression stresses both into a bending component ( as typified by angle $\beta°$ in FIG. 12) and to twisting components ( as typified by angle $\gamma°$ and $\delta°$ in FIG. 12) and determining the overall size of a desired stent, determination of the optimum materials as well as the sizes of the various integral components making up the stent becomes straightforward. Specifically, the diameter and length of torsion lengths, apex portion dimensions and the number of torsion segments around the stent may then be determined.

Figure 13B:
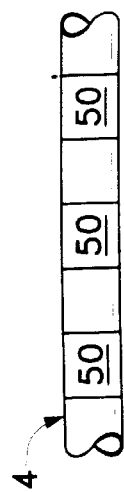
FIG. 13B diagrammatically shows a further stent-member construction for supporting the graft member.
Figure 13A:
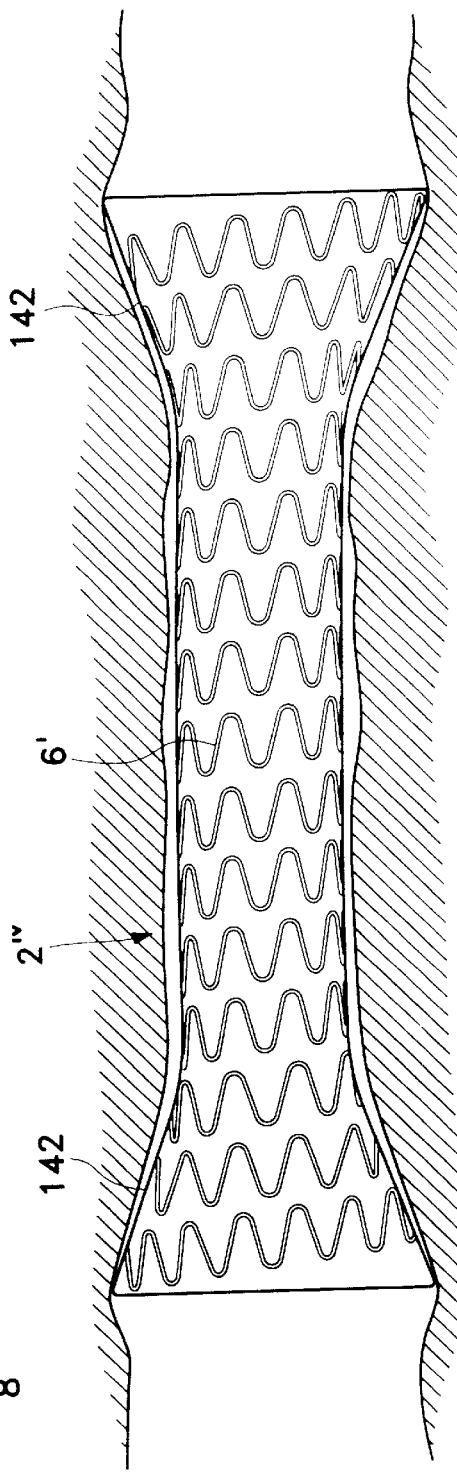
FIG. 13A diagrammatically shows a further stent-member of the present invention with flared ends (the coupling tape drawn back to more clearly show the helically wound undulating stent configuration).

Referring to FIG. 13A, a stent-graft$^{iv}$ differing from stent-graft 1 in graft support structure is shown. Stent-graft $2^{iv}$ includes stent member 6' which is the same as stent member 6 with the exception that it includes flared end portions 142 at one or both ends. Flared end portions 142 provide secure anchoring of the resulting stent-graft $2^{iv}$ against the vessel wall and prevents the implant from migrating downstream. In addition, flared end portions 142 provide a tight seal against the vessel so that the blood is channeled through the lumen rather than outside the graft. The undulating structure may vary in spacing to allow the helical turns to maintain their phased relationship as discussed above. Although a linking member between the continuous helical turns is not shown, such structure preferably is included to maintain the alignment of the apexes as discussed above.

The graft support structure also may be made by forming a desired structural pattern out of a flat sheet. The sheet may then be rolled to form a tube. The stent also may be machined from tubing. If the chosen material is nitinol, careful control of temperature during the machining step may be had by EDM (electro-discharge-machining), laser cutting, chemical machining, or high pressure water cutting. As shown in FIG. 13B, the stent-member (graft support structure) may comprise multiple tubular members or sections 50, each coupled to the graft-member 4 with a coupling member as described above. Tubular members or sections 50 may have various construction and, thus, may be configured to have the same construction as the stent-member 6 shown in FIGS. 1–11, for example. Tubular members also may be directly coupled to each other (e.g., with bridging element(s) extend between adjacent sections as would be apparent to one of ordinary skill) or, indirectly coupled to each other through their interconnection with the graft member.

Figure 14A:
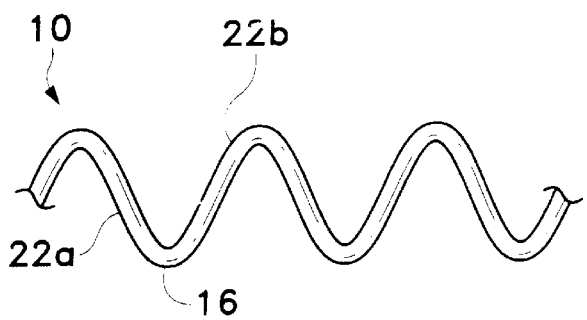
FIGS. 14A, 14B, 14C, 14D, 14E, and 14F are plan views of unrolled stent forms suitable for use in the invention.
Figure 14B:
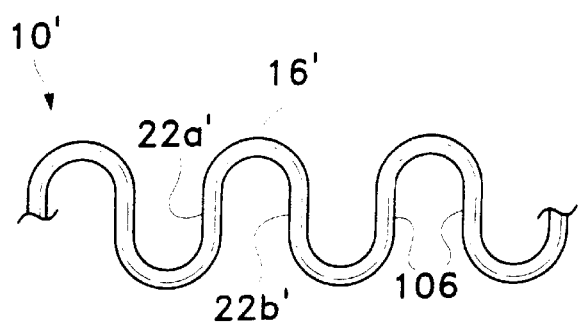
Figure 14C:
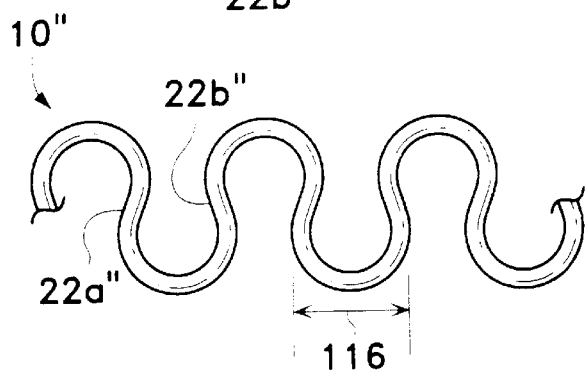
Figure 14D:
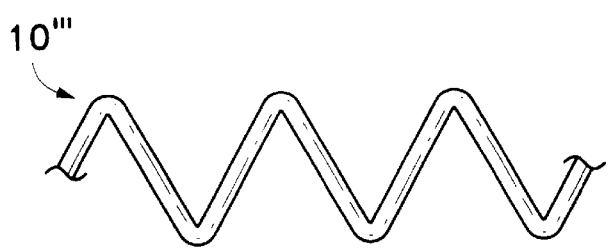
Figure 14E:
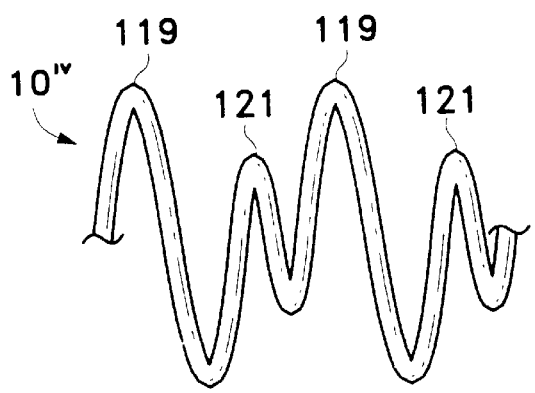
Figure 14F:
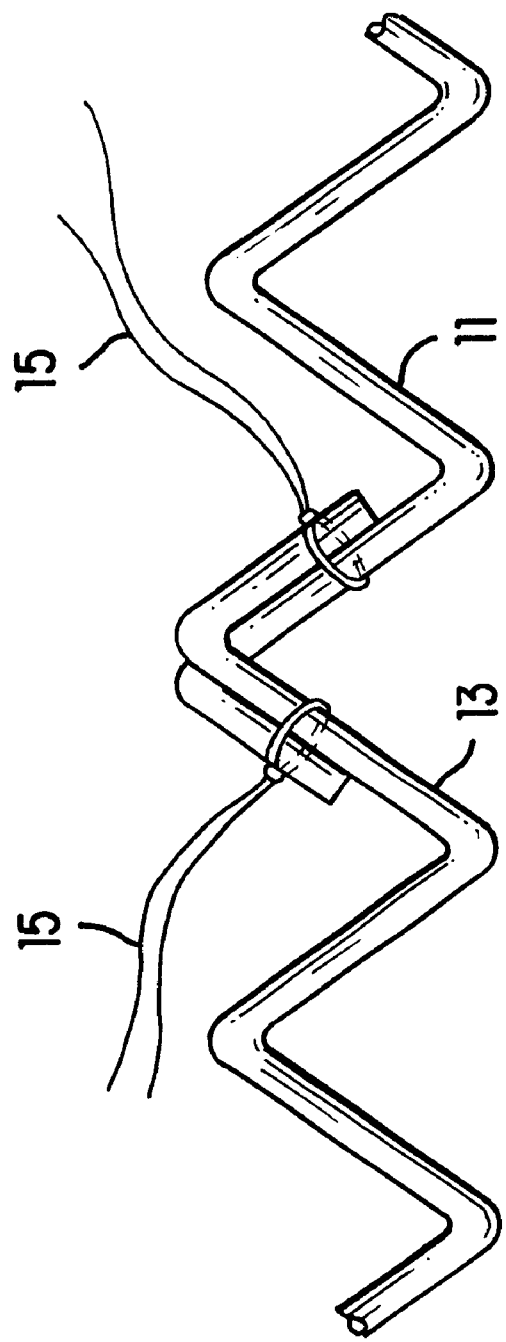

Referring to FIGS. 14A–F, various undulation configurations suitable for the present invention are shown. FIG. 14A shows the sinusoidal shaped undulating member 10 described above. Adjacent torsion arms 22a & b are not parallel. FIG. 14B shows an undulating member 10' having generally U-shaped undulations or torsion members where the torsion arms are generally parallel. FIG. 14C shows a further variation where undulating member 10" includes ovoid shaped undulations or torsion segments. In this variation, adjacent torsion arms 22" a & b are again not parallel, but generally form an open-ended oval. FIG. 14D shows another variation where undulating member 10'" includes V-shaped torsion members. In this variation, the adjacent torsion arms 120 form a relatively sharp angle at the respective apex portions. FIG. 14E shown undulating member $10^{iv}$ in which adjacent undulations have different amplitudes. The peaks of the large amplitude torsion segments 119 may be lined up "out of phase" or "peak to peak" with small or large amplitude torsion segments 110, 121, respectively, in the adjacent turn of the helix or may be positioned "in phase" similar to those discussed with regard to FIGS. 1A and B above. The configurations shown in FIGS. 14A–14E are exceptionally kink-resistant and flexible when flexed along the longitudinal axis of the stent-member. FIG. 14F shows a stent formed from sections 11 and 13 which are connected to one another by sutures 15.

As discussed above, the stent member preferably is oriented coaxially with the tubular graft member. Although the stent member may be placed within the graft member, it preferably is placed on the outer surface of the graft member so that a relatively smooth graft wall interfaces with the blood. In certain configurations, an additional graft member may be placed on the outer surface of the stent-graft illustrated in the drawings. When the multiple graft structure is utilized, the stent structure should have the strength and flexibility to urge the graft tubing firmly against the vessel wall so that the graft member conforms with the inner surface of the vessel wall. In addition, the graft member preferably is impermeable to blood at normal or physiologic blood pressures. The impermeability makes the stent-graft suitable for shunting and thereby hydraulically isolating aneurysms.

The scope of materials suitable for the stent and graft members and the linking member as well as deployment mechanisms will be discussed in detail, below.

Stent Materials

The stent member is constructed of a reasonably high strength material, i.e., one which is resistant to plastic deformation when stressed. Preferably, the stent member comprises a wire which is helically wound around a mandrel having pins arranged thereon so that the helical turns and undulations can be formed simultaneously. Other constructions also may be used. For example, an appropriate shape may be formed from a flat stock and wound into a cylinder or a length of tubing formed into an appropriate shape.

In order to minimize the wall thickness of the stent-graft, the stent material should have a high strength-to-volume ratio. Use of designs as depicted herein provides stents which may be longer in length than conventional designs. Additionally, the designs do not suffer from a tendency to twist (or helically unwind) or to shorten as the stent-graft is deployed. As will be discussed below, materials suitable in these stents and meeting these criteria include various metals and some polymers.

A percutaneously delivered stent-graft must expand from a reduced diameter, necessary for delivery, to a larger deployed diameter. The diameters of these devices obviously vary with the size of the body lumen into which they are placed. For instance, the stents of this invention may range in size from 2.0 mm in diameter (for neurological applications) to 40 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Typical expansion ratios for use with the stents-grafts of the invention typically are in the range of about 2:1 to about 4:1 although the invention is not so limited. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thickness of about 0.002 inches to 0.005 inches is usually sufficient. For the larger stents, the appropriate thickness for the stent flat stock may be somewhat thicker, e.g., 0.005 to 0.020 inches.

The stent-graft is fabricated in the expanded configuration. In order to reduce its diameter for delivery the stent-graft would be folded along its length, similar to the way in which a PCTA balloon would be folded. It is desirable, when using super-elastic alloys which also have temperature-memory characteristics, to reduce the diameter of the stent at a temperature below the transition-temperature of the alloys. Often the phase of the alloy at the lower temperature is somewhat more workable and easily formed. The temperature of deployment is desirably above the transition temperature to allow use of the super-elastic properties of the alloy.

There are a variety of disclosures in which super-elastic alloys such as a nitinol are used in stents. See, U.S. Pat. Nos. 4,503,569 to Dotter, 4,512,338 to Balko et al., 4,990,155 to Wilkoff, 5,037,427 to Harada, et al., 5,147,370 to Mac-Namara et al., 5,211,658 to Clouse, and 5,221,261 to Termin et al. None of these references suggest a device having discrete individual, energy-storing torsional members.

Jervis, in U.S. Pat. Nos. 4,665,906 and 5,067,957, describes the use of shape memory alloys having stress-induced martensite properties in medical devices which are implantable or, at least, introduced into the human body.

It should be clear that a variety of materials variously metallic, superelastic alloys, and preferably nitinol, are suitable for use in these stents. Primary requirements of the materials are that they be suitably springy even when fashioned into very thin sheets or small diameter wires. Various stainless steels which have been physically, chemically, and otherwise treated to produce high springiness are suitable, as are other metal alloys such as cobalt chrome alloys (e.g., ELGILOY), platinum/tungsten alloys, and especially the nickel-titanium alloys generically known as "nitinol".

Nitinol is especially preferred because of its "super-elastic" or "pseudo-elastic" shape recovery properties, i.e., the ability to withstand a significant amount of bending and flexing and yet return to its original form without deformation. These metals are characterized by their ability to be transformed from an austenitic crystal structure to a stress-induced martensitic structure at certain temperatures, and to return elastically to the austenitic shape when the stress is released. These alternating crystalline structures provide the alloy with its super-elastic properties. These alloys are well known but are described in U.S. Pat. Nos. 3,174,851, 3,351,463, and 3,753,700. Typically nitinol will be nominally 50.6% (±0.2%) Ni with remainder Ti. Commercially available nitinol materials usually will be sequentially mixed, cast, formed, and separately cold-worked to 30–40%, annealed, and stretched. Nominal, ultimate yield strength values for commercial nitinol are in the range of 30 psi and for Young's modulus are about 700 Kbar.

The '700 patent describes an alloy containing a higher iron content and consequently has a higher modulus than the Ni—Ti alloys.

Nitinol is further suitable because it has a relatively high strength to volume ratio. This allows the torsion members to be shorter than for less elastic metals. The flexibility of the stent-graft is largely dictated by the length of the torsion segments and/or torsion arms. The shorter the pitch of the device, the more flexible the stent-graft structure can be made. Materials other than nitinol are suitable. Spring tempered stainless steels and cobalt-chromium alloys such as ELGILOY are also suitable as are a wide variety of other known "super-elastic" alloys.

Although nitinol is preferred in this service because of its physical properties and its significant history in implantable medical devices, we also consider it also to be useful in a stent because of its overall suitability with magnetic resonance imaging (MRI) technology. Many other alloys, particularly those based on iron, are an anathema to the practice of MRI causing exceptionally poor images in the region of the alloy implant. Nitinol does not cause such problems.

Other materials suitable as the stent include certain polymeric materials, particularly engineering plastics such as thermotropic liquid crystal polymers ("LCP's"). These polymers are high molecular weight materials which can exist in a so-called "liquid crystalline state" where the material has some of the properties of a liquid (in that it can flow) but retains the long range molecular order of a crystal. There term "thermotropic" refers to the class of LCP's which are formed by temperature adjustment. LCP's may be prepared from monomers such as p,p'-dihydroxy-polynuclear-aromatics or dicarboxy-polynuclear-aromatics. The LCP's are easily formed and retain the necessary interpolymer attraction at room temperature to act as high strength plastic artifacts as are needed as a foldable stent. They are particularly suitable when augmented or filled with fibers such as those of the metals or alloys discussed below. It is to be noted that the fibers need not be linear but may have some preforming such as corrugations which add to the physical torsion enhancing abilities of the composite.

Linking Member Materials

Flexible link 20, which is slidably disposed between adjacent turns of the helix may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred in this invention is the use of polymeric biocompatible filaments. Synthetic polymers such as polyethylene, polypropylene, polyurethane, polyglycolic acid, polyesters, polyamides, their mixtures, blends and copolymers are suitable; preferred of this class are polyesters such as, polyethylene terephthalate including DACRON and MYLAR and polyaramids such as KEVLAR, polyfluorocarbons such as polytetrafluoroethylene with and without copolymerized hexafluoropropylene, TEFLON or ePTFE, and porous or nonporous polyurethanes. Natural materials or materials based on natural sources such as collagen may also be used in this service.

Graft Member Materials

The tubular component or graft member of the stent-graft may be made up of any material which is suitable for use as a graft in the chosen body lumen. Many graft materials are known, particularly known are those used as vascular graft materials. For instance, natural materials such as collagen may be introduced onto the inner surface of the stent and fastened into place. Desirable collagen-based materials include those described in U.S. Pat. No. 5,162,430, to Rhee et al, and WO 94/01483 (PCT/US93/06292), the entirety of which are incorporated by reference. Synthetic polymers such as polyethylene, polypropylene, polyurethane, polyglycolic acid, polyesters, polyamides, their mixture, blends, copolymers, mixtures, blends and copolymers are suitable, preferred of this class are polyesters such as polyethylene terephthalate including DACRON and MYLAR and polyaramids such as KEVLAR, polyfluorocarbons such as polytetrafluoroethylene (PTFE) with and without copolymerized hexafluoropropylene, expanded or not-expanded PTFE, and porous or nonporous polyurethanes. Especially preferred in this invention are the expanded fluorocarbon polymers (especially PTFE) materials described in British Pat. Nos. 1,355,373, 1,506,432, or 1,506,432 or in U.S. Pat. Nos. 3,953,566, 4,187,390, or 5,276,276, the entirety of which are incorporated by reference.

Included in the class of preferred fluoropolymers are polytetrafluoroethylene (PTFE), fluorinated ethylene propylene (FEP), copolymers of tetrafluorethylene (TFE), and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular protheses, is expanded PTFE.

In addition, one or more radio-opaque metallic fibers, such as gold, platinum, platinum-tungsten, palladium, platinum-iridium, rhodium, tantalum, or alloys or composites of these metals like may be incorporated into the device, particularly, into the graft, to allow fluoroscopic visualization of the device.

The tubular component may also be reinforced using a network of small diameter fibers. The fibers may be random, braided, knitted or woven. The fibers may be imbedded in the tubular component, may be placed in a separate layer coaxial with the tubular component, or may be used in a combination of the two.

A preferred material for the graft and coupling members is porous expanded polytetrafluorethylene. An FEP coating is one preferred adhesive that is provided on one side of the coupling member.

Manufacture of the Stent-Graft

The following example is provided for purposes of illustrating a preferred method of manufacturing a stent-graft constructed according to the present invention which in this example case is the stent-graft shown in FIGS. 1–6. It should be noted, however, that this example is not intended to limit the invention.

The stent member wire is helically wound around a mandrel having pins positioned thereon so that the helical structure and undulations can be formed simultaneously. While still on the mandrel, the stent member is heated to about 460° F. for about 20 minutes so that it retains its shape.

Wire sizes and materials may vary widely depending on the application. The following is an example construction for a stent-graft designed to accommodate 6 mm diameter vessel lumen. The stent member comprises a nitinol wire (50.8 atomic % Ni) having a diameter of about 0.007 inch. In this example case, the wire is formed to have sinusoidal undulations, each having an amplitude measured peak-to-peak of about 0.100 inch and the helix is formed with a pitch of about 10 windings per inch. The inner diameter of the helix (when unconstrained) is about 6.8 mm. The nitinol wire may be polished if desired. If a polished wire is desired, the wire is fed through an electrolytic bath having an applied potential to electrolytically clean, passivate and polish the wire. The polishing reduces the availability of surface nickel for extraction or corrosion. Suitable electrolytic treating materials for the bath are commercially available. One such source of a commercially available electrolytic treating material is NDC (Nitinol Devices and Components. The linking member can be arranged as shown in the drawings and may have a diameter of about 0.006 inch.

In this example, the graft member is porous expanded polytetrafluorethylene (PTFE), while the coupling member is expanded PTFE coated with FEP. The coupling member is in the form of a flat ribbon (as shown in the illustrative embodiments) that is positioned around the stent and graft members as shown in FIGS. 1–3. The side of the coupling member or ribbon that is FEP coated faces the graft member to secure it to the graft member. The intermediate stent-graft construction is heated to allow the materials of the ribbon and graft member to merge and self-bind as will be described in more detail below.

The FEP-coated porous expanded PTFE film used to form the ribbon shaped coupling member preferably is made by a process which comprises the steps of:

(a) contacting a porous PTFE film with another layer which is preferably a film of FEP or alternatively of another thermoplastic polymer.

(b) heating the composition obtained in step (a) to a temperature above the melting point of the thermoplastic polymer;

(c) stretching the heated composition of step (b) while maintaining the temperature above the melting point of the thermoplastic polymer, and (d) cooling the product of step (c)

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

Figure 1C:
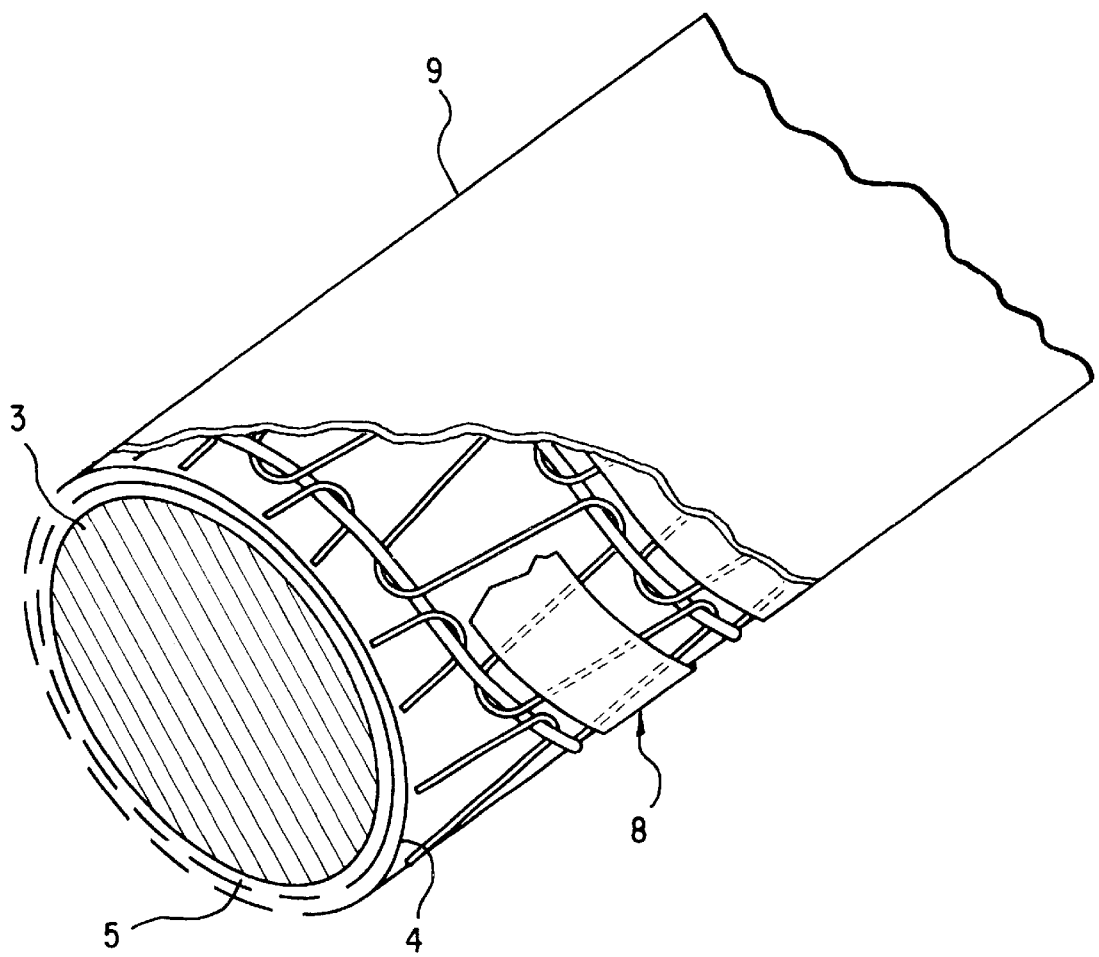
FIG. 1C is an enlarged perspective view of a portion of the stent-graft shown in FIG. 1A mounted on a cushioned mandrel.

The thin wall expanded PTFE graft used to construct this example contains an inner tube of PTFE and an outer helical wrap of PTFE. The graft was about 0.1 mm (0.004 in) thickness and had a density of about 0.5 g/cc. The microstructure of the porous expanded PTFE contained fibrils of about 25 micron length. A 3 cm length of this graft material was placed on a mandrel the same diameter as the inner diameter of the graft. Advantageously, as shown in FIG. 1C, a cushioning layer 5 was placed on the mandrel 3 prior to placement of the graft 4. The nitinol stent member having about a 3 cm length was then carefully fitted over the center of the thin wall graft 4 and extended to its desired length. Any struts out of phase should be placed in phase prior to applying the coupling member.

The stent-member was then provided with a ribbon shaped coupling member comprised of the FEP coated film as described above. The coupling member was helically wrapped around the exterior surface of the stent-member as shown in FIGS. 1–6. The uniaxially-oriented fibrils of the microstructure of the helically-wrapped ribbon were helically-oriented about the exterior of stent surface. The ribbon shaped coupling member was oriented so that its FEP-coated side faced inward and contacted the exterior of surface of the stent-member. This ribbon surface was exposed to the outward facing surface of the thin wall graft member exposed through the openings in the stent member.

Advantageously, an outer, multi-component sheath 9, formed by a longitudinally slit tube of non-adhering PTFE and an outer helical wrap of non-adhering PTFE is placed around the stent-graft-coupling member assembly to compress the assembly onto the mandrel (FIG. 1C). Alternatively, sheath 9 may be formed by helically wrapping PTFE around the stent-graft-coupling assembly without the longitudinally slit tube.

The mandrel assembly was placed into an oven set at 315° C. for a period of 15 minutes after which the film-wrapped mandrel was removed from the oven and allowed to cool. Following cooling to approximately ambient temperature, the mandrel, as well as the cushioning layer and outer compression tube, was removed from the resultant stent-graft. The amount of heat applied was adequate to melt the FEP-coating on the porous expanded PTFE film and thereby cause the graft and coupling members to adhere to each other. Thus, the graft member was adhesively bonded to the inner surface of helically-wrapped coupling member 8 through the openings between the adjacent wires of the stent member. The combined thickness of the luminal and exterior coverings (graft and coupling members) and the stent member was about 0.4 mm.

The stent-graft was then folded in order to prepare it for delivery. To accomplish this a stainless steel wire which was a couple of inches longer than the stent-graft was inserted through the lumen of the stent-graft. The stent-graft was flattened and the stainless steel wire positioned at one end of the stent-graft. A second stainless wire of about the same length was placed on the outer surface of the stent-graft adjacent to the first stainless steel wire. The wires were then mounted together into a fixture, tensioned and then rotated, thereby folding the stent-graft as shown in FIGS. 15C & D which will be discussed in more detail below. As the stent-graft rotates it is pressed into a "C" shaped elongated stainless steel clip in order to force it to roll upon itself. The folded stent-graft is then advanced along the wire out of the clip into a glass capture tube. A removable tether line, which is used to constrain the stent-graft in the rolled configuration for delivery, as will be discussed in more detail below, is applied to the stent-graft at this point by gradually advancing the stent-graft out of the capture tube and lacing the tether line through the stent-graft structure. After this step is completed, the stent-graft is pulled off of the first wire and transferred onto the distal end of the catheter shaft or tubing for delivery.

Prior to folding, the stent-graft was cooled to about −30° C. so that the nitinol was fully martensitic and, thus, malleable. This is done to allow the stent-graft to be more easily folded. Cooling is accomplished by spray soaking the graft with chilled gas such as tetrafluroethane. Micro-Dust™ dry circuit duster manufactured by MicroCave Corporation (Conn) provides suitable results. The spray canister was held upside down to discharge the fluid as a liquid onto the stent-graft.

Deployment of the Stent-Graft

The stent-graft may be delivered percutaneously, typically through the vasculature, after having been folded to a reduced diameter. Once reaching the intended delivery site, it is expanded to form a lining on the vessel wall.

When a stent-graft having torsion members, as described above, is folded, crushed, or otherwise collapsed, mechanical energy is stored in torsion in those members. In this loaded state, the torsion members have a torque exerted by the torsion members as folded down to a reduced diameter must be restrained from springing open. The stent-member preferably has at least one torsion member per fold. The stent-graft is folded along its longitudinal axis and restrained from springing open. The stent-graft is then deployed by removing the restraining mechanism, thus allowing the torsion members to spring open against the vessel wall. The stent grafts of this invention are generally self-opening once deployed. If desired, an inflatable balloon catheter or similar means to ensure full opening of the stent-graft may be used under certain circumstances.

The attending physician will select an appropriately sized stent-graft. Typically, the stent-graft will be selected to have an expanded diameter of up to about: 10% greater than the diameter of the lumen at the deployment site.

FIG. 15A diagrammatically illustrates a folding sequence for folding a stent-graft constructed according to the present invention. The stent-graft, generally designated with reference numeral 200 is positioned about a guidewire 232 and folded into a loose C-shaped configuration. FIG. 15B shows a diagrammatic perspective view of the resulting folded stent-graft. FIGS. 15C & E show further folding sequences. FIGS. 15D & F show diagrammatic perspective views of the resulting folded stent-grafts showing the rolled and triple lobed configurations, respectively. The rolled configuration is preferred.

Figure 16A:
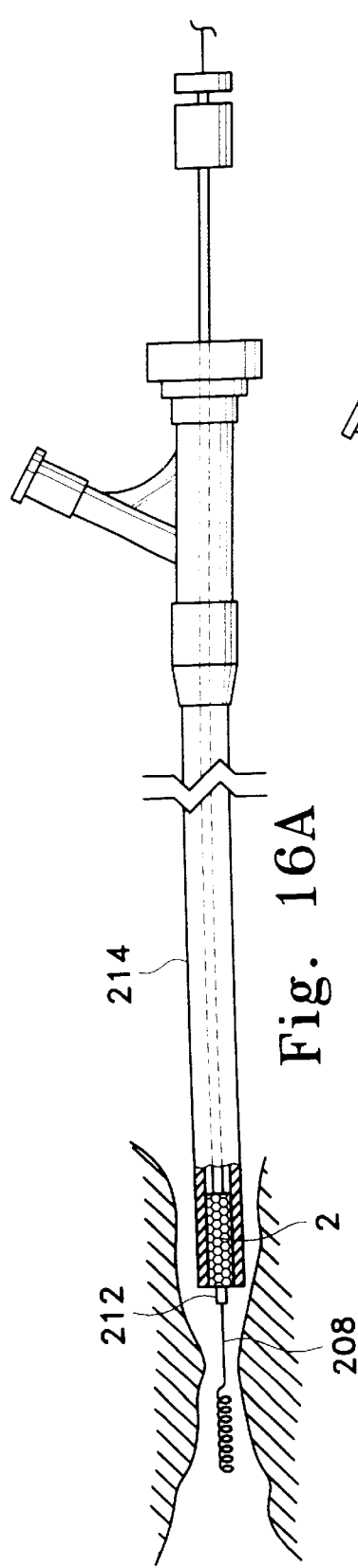
FIGS. 16A, 16B, and 16C diagrammatically show a procedure for deploying the stent-grafts using an external sleeve.
Figure 16B:
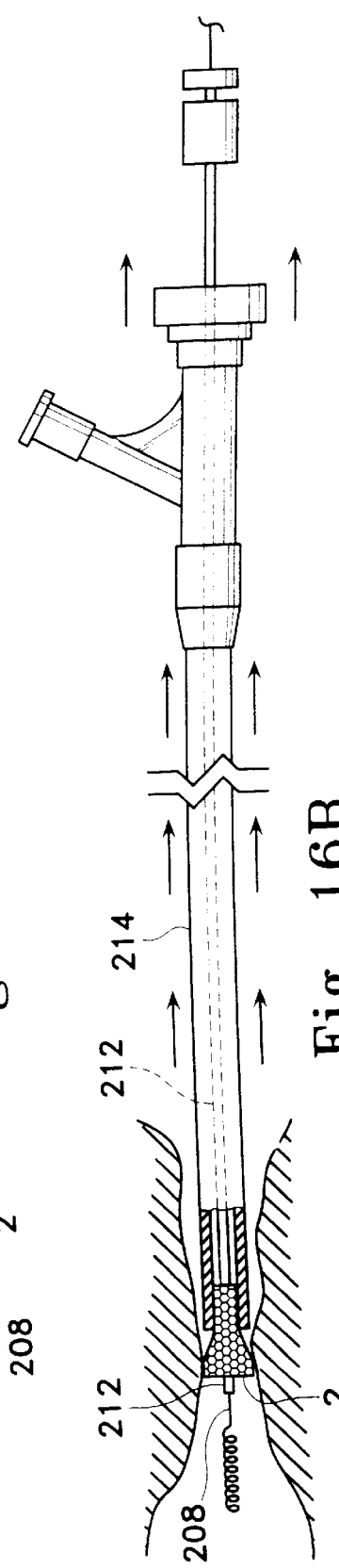
Figure 16C:
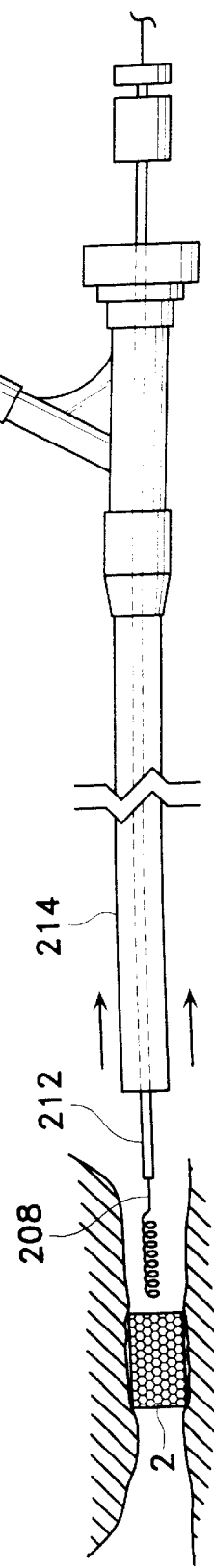

FIGS. 16A–16C diagrammatically illustrate deployment procedures for the present invention. FIG. 16A shows an example target site having a narrowed vessel lumen. A guidewire 208 having a guide tip has been directed to the site using known techniques. The stent-graft 210 is mounted on guidewire tubing 212 inside outer sliding sheath 214 after having been folded in the manner discussed above. The outer sliding sheath 214 binds the compressed stent-graft 210 in place until released.

FIG. 16B shows placement of the stent-graft 120 at the selected site by sliding the stent-graft over the guidewire all together with the guidewire tubing 212 and the outer sliding sheath 214. The stent-graft is deployed by holding the guidewire tubing 212 in a stationary position while withdrawing the outer sliding sheath 214. FIG. 16B shows the stent-graft partially deployed, while FIG. 16C shows the stent-graft fully deployed after the guidewire tubing and the outer sliding sheath have been fully retracted.

FIGS. 17A–C, 18A–C, and 19A–C show deployment variations for deploying a stent-graft constructed according to the present invention. These methods involve the use of a control line or tether line which maintains the stent or stent-graft in a folded configuration until release.

Figure 17C:
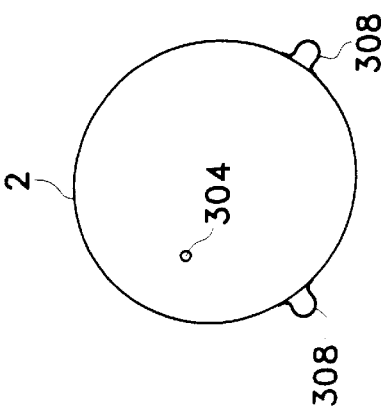
FIGS. 17A and 18A are partial perspective views of folded stent-grafts.
FIGS. 17B, 18C, 18B, and 18C are end views of the stent-grafts shown in FIGS. 17A and 18A in folded and open states.
Figure 18C:
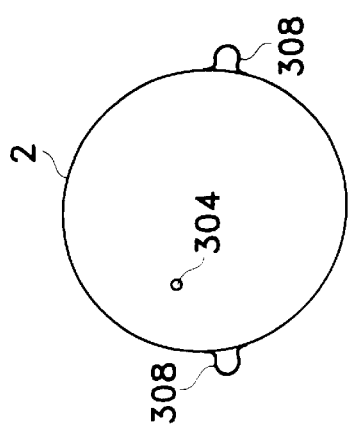
Figure 17B:
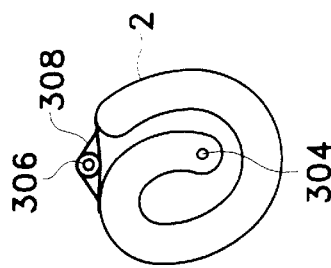
Figure 18B:
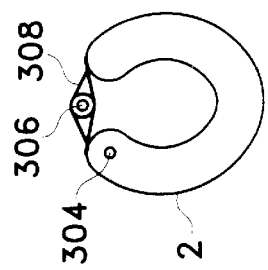
Figure 17A:
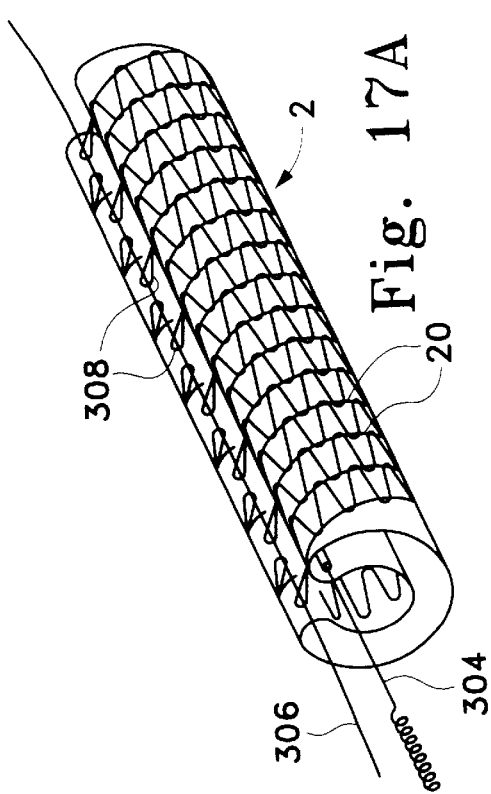
Figure 18A:
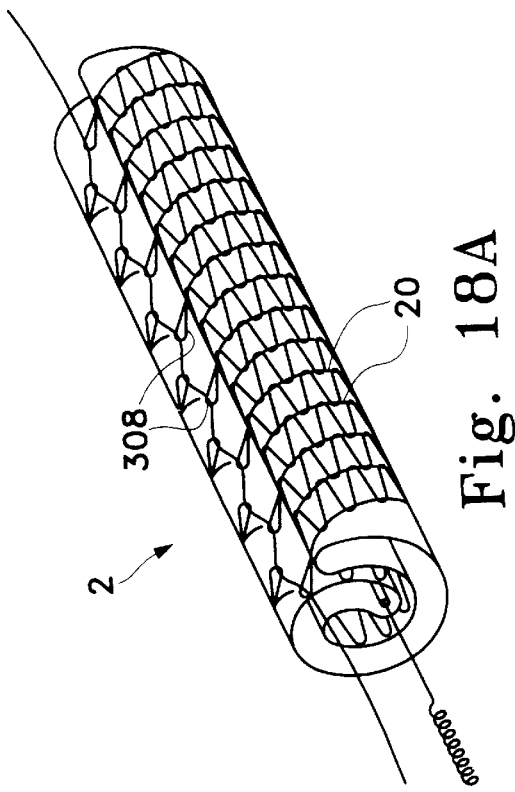

Referring to FIGS. 17A & B, diagrammatically represented stent-graft 302 is shown folded about guidewire 304 so that, when deployed, the guidewire 304 is within stent-graft 302. A tether wire 306 is passed through loops 308 which preferably are formed by pulling the linking member discussed above away from the stent structure. When tether wire 306 is removed by sliding it axially along the stent-graft and out of loops 308, the stent-graft unfolds into a generally cylindrical shape. (FIG. 17C). Referring to, FIGS. 18A & B stent-graft 302 is shown in a rolled pre-deployment configuration. In this case, guidewire 304 is inside the stent. When expanded by removal of tether wire 306, the stent-graft assumes the form shown in FIG. 18C.

FIGS. 19A–C diagrammatically show additional procedures for deploying a stent-graft of the present invention using a percutaneous catheter assembly 314. Referring to FIG. 19A catheter assembly 314 has been inserted to a selected site within a body lumen. Stent-graft 312 is folded about guidewire 319 and guidewire tube 318 held axially in place prior to deployment by distal barrier 320 and proximal barrier 322. The distal and proximal barriers typically are affixed to the guidewire tube 318. Tether wire 306 is extends through loops 308 proximally through the catheter assembly's 314 outer jacket 324 through to outside the body. FIG. 19B shows partial removal of tether wire 306 from loops 308 to partially expand the stent-graft 312 onto the selected site. FIG. 19C shows complete removal of the tether wire, the loops and retraction of the catheter assembly 314 from the interior of the stent-graft which is fully expanded.

Figure 20:
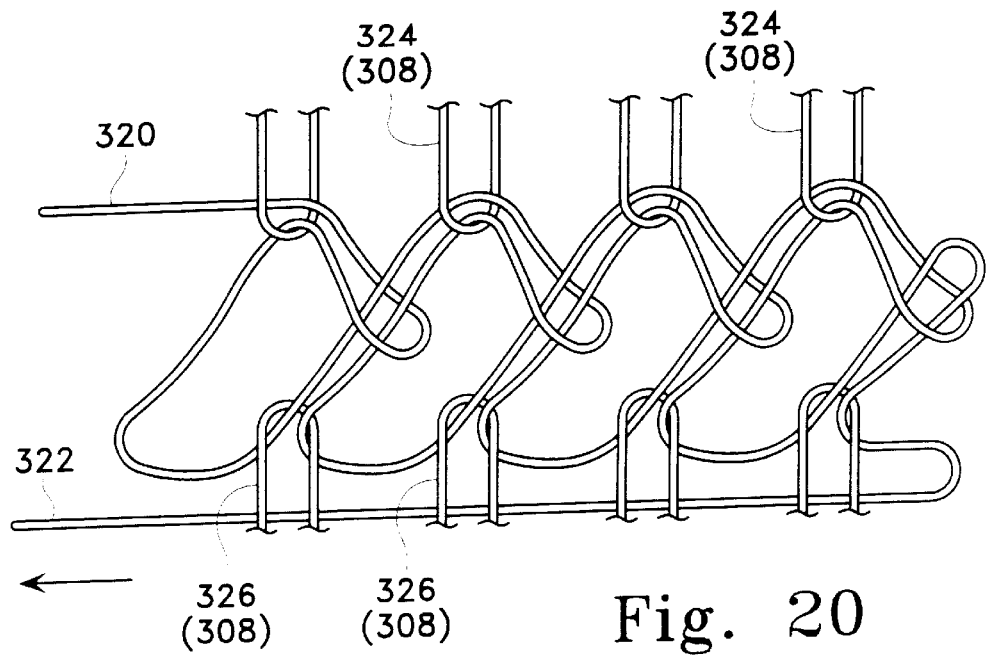
FIG. 20 show a close-up view of a stent fold line using a preferred sack knot in the slip line.

FIG. 20 shows a close-up of a stent fold line having the familiar herringbone pattern of the preferred "sack knot" used to close the fold in the stent. This knot is the one used to hold, e.g., burlap sacks of feed grain closed prior to use and yet allow ease of opening when the sack is to be opened. In this variation, the slip line has a fixed end 320 and a release end 322. Loops of the slip line pass through the eyelets 324 on the side of the stent fold associated with the fixed end 320 and are held in place by eyelets 326 on the side of the stent fold associated with the release end 322. The fixed end 320 is not typically tied to the stent so to allow removal of the slip line after deployment. The eyelets 324 and 326 are desirable but optional. The eyelets 324 and 326 may be wire or polymeric thread or the like tied to the stent structure at the edge of the stent fold. If so desired, the loops may be dispensed with and the slip line woven directly into the stent structure. The self-expanding stent may be deployed by pulling axially on release end 322 as shown by the arrow in the drawing.

Figure 21:
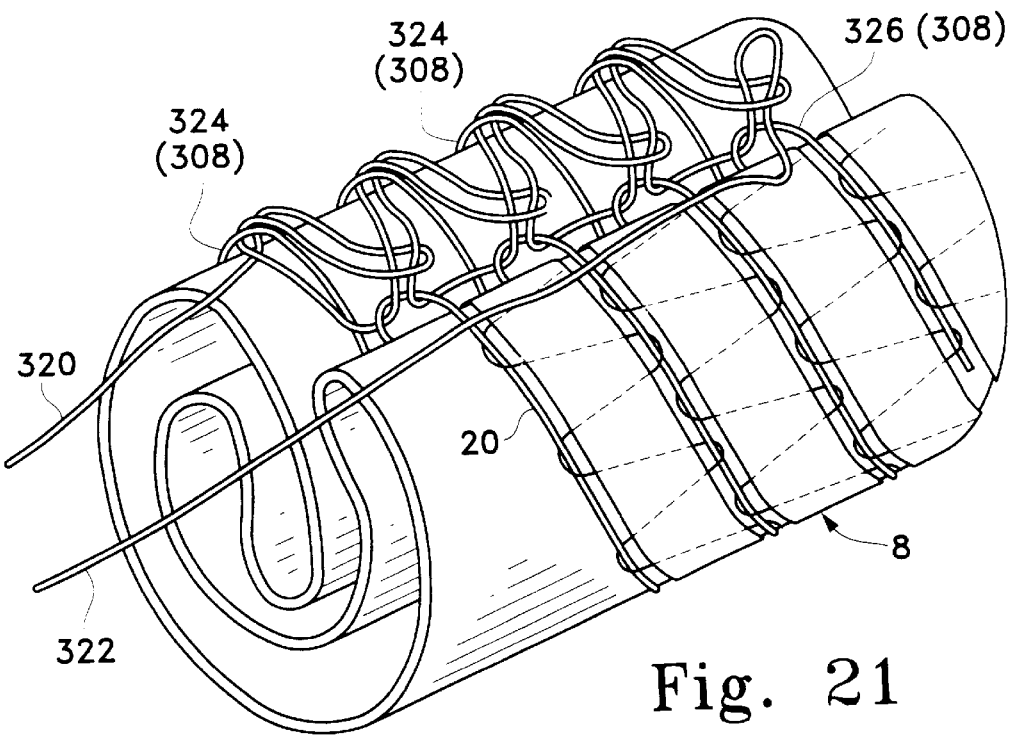
FIG. 21 is a diagrammatic perspective view of a folded stent-graft held in a position by a tether line and a sack knot as illustrated in FIG. 20.

FIG. 21 is a diagrammatic perspective view of a folded stent-graft using the knot shown in FIG. 20. FIG. 21 shows the use of a single stent fold similar in configuration to those described above. As was shown in FIG. 20, the fixed end portion 320 of the slip line is associated with a row of eyelets 324 which preferably are formed by pulling local portions of linking member 20 away from the fold line, threading the slip line therethrough and then releasing the respective portion of the linking member. Alternatively, the eyelets may be tied or otherwise fixed to the stent. The release end 322 is associated with the other row of eyelets 326.

Although stent-graft deployment is described using a catheter for percutaneous delivery, it should be understood that other deployment techniques may be used. The folded stent-graft may also be deployed through artificial or natural body openings with a sheath or endoscopic delivery device, for example, and perhaps, without a guidewire. Similarly, the stent-graft may be delivered manually during a surgical procedure.

The stent-graft of the present invention may be used, for example, to reinforce vascular irregularities and provide a smooth nonthrombogenic interior vascular surface for diseased areas in blood vessels, or to increase blood flow past a diseased area of a vessel by mechanically improving the interior surface of the vessel. The inventive stent-graft is especially suitable for use within smaller vessels between 2 mm and 6 mm in diameter but is equally suitable for significantly larger vessels. The inventive stent-graft may be self-expanded so that it may be percutaneously delivered in a folded state on an endovascular catheter or via surgical or other techniques and then expanded. The stent-graft construction described above also provides a variable length stent-graft. This is especially advantageous during implantation procedures.

Currently, it is difficult for a physician to accurately determine anatomical distances due to vessel tortuosity in different planes which often occurs in aorta/iliac aneurysmal disease. Also, it is important for the physician to accurately measure distances when placing an endovascular stent-graft so the entire aneurysmal length is covered, yet important vessel branches are not occluded. The stent-graft design of the present invention allows the physician to adjust its length during deployment allowing more accurate placement of the device.

The following example illustrates the steps involved in placing a variable-length stent-graft into a patient's anatomy. In this example, stent-graft is a single tubular design, placed into the thoracic aorta 70, and will be located between the renal arteries and the T-7 artery. The direction of deployment will be from renals 'upstream' to the T-7 artery. The device will be supplied in its longest state with shortening capability during deployment (the inverse where a copressed stent-graft is deployed also is possible).

The physician estimates the length required, and chooses a device which is at least as long, and usually slightly longer than the estimated length.

Figure 22:
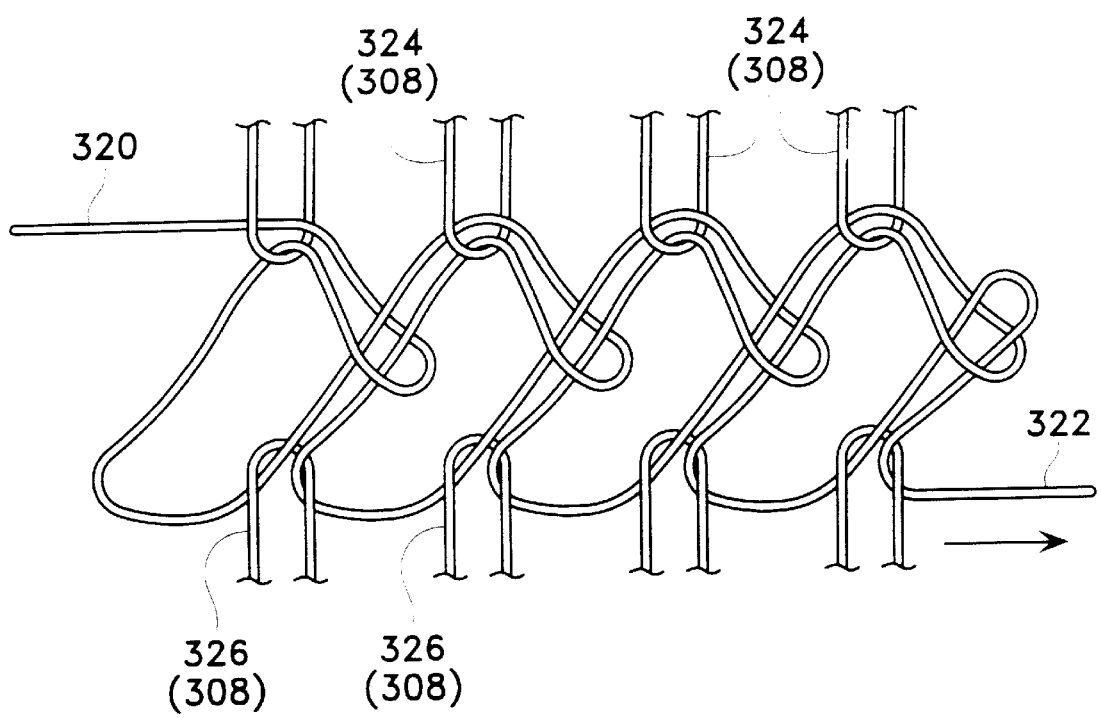
FIGS. 22, 23, 24, and 25 are diagrammatic sequential illustrations of a further deployment procedure.

The stent-graft is inserted through an introducer as is conventional in the art. It is advanced until its distal ends 2a is located as desired near the renal arteries (72) (FIG. 22). At this point, the proximal end of the stent-graft would be located at or past the T-7 artery (74).

Figure 23:
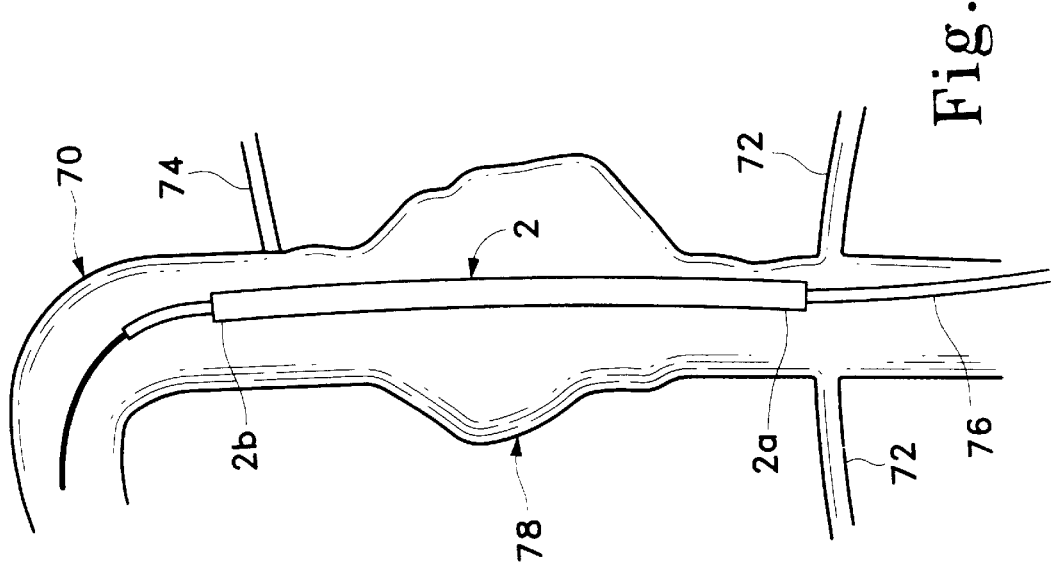
Figure 26:
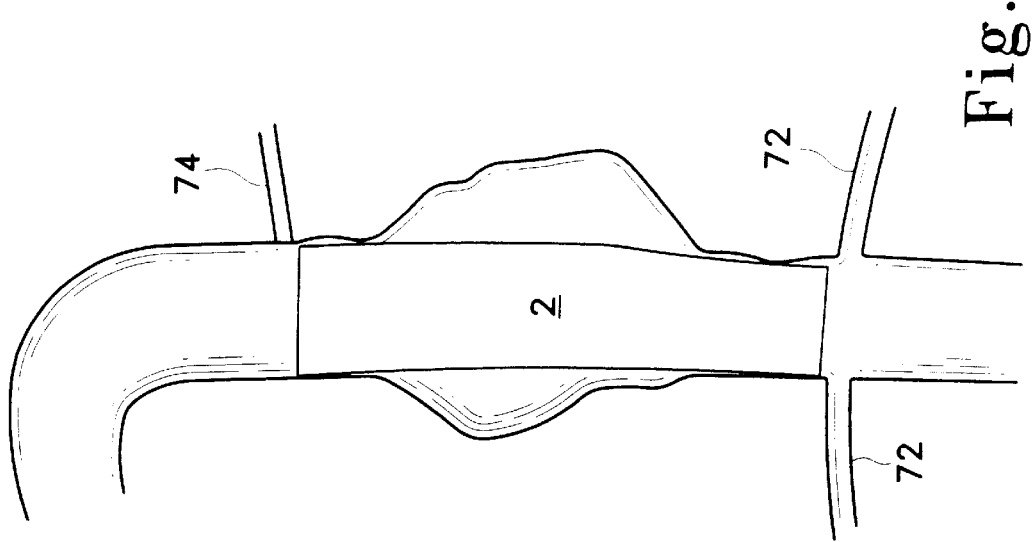

The stent-graft deployment is initiated slowly, distal to proximal ('downstream to upstream') (FIG. 23) while watching the proximal end location on fluoroscopy.

As needed, the delivery catheter 76, which is of conventional construction, would be pulled toward the operator, shortening the stent-graft to keep the proximal end in the correct location. This shortening can occur as long as the portion of the stent-graft being compressed is within the aneurysm 78.

Figure 24:
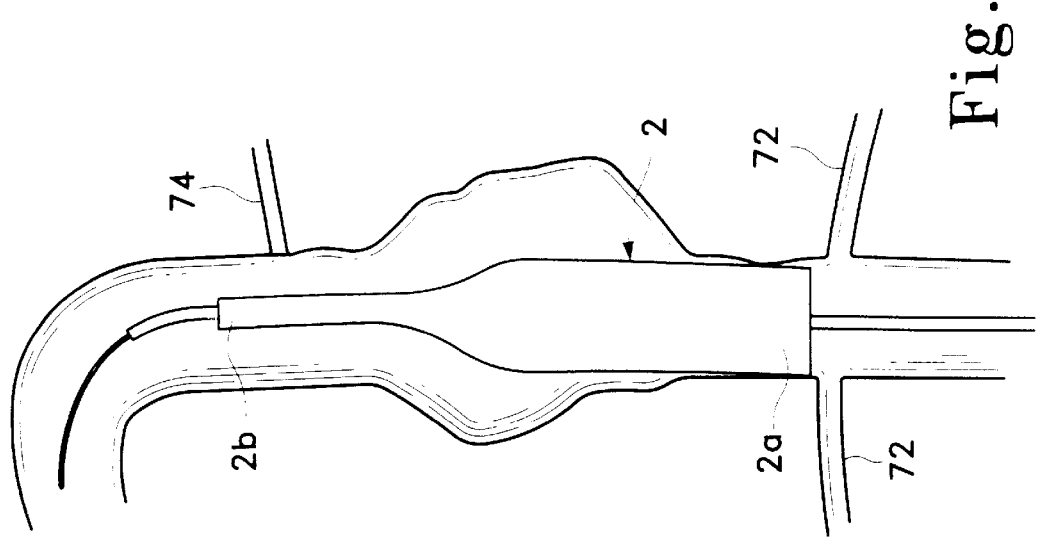
Figure 25:
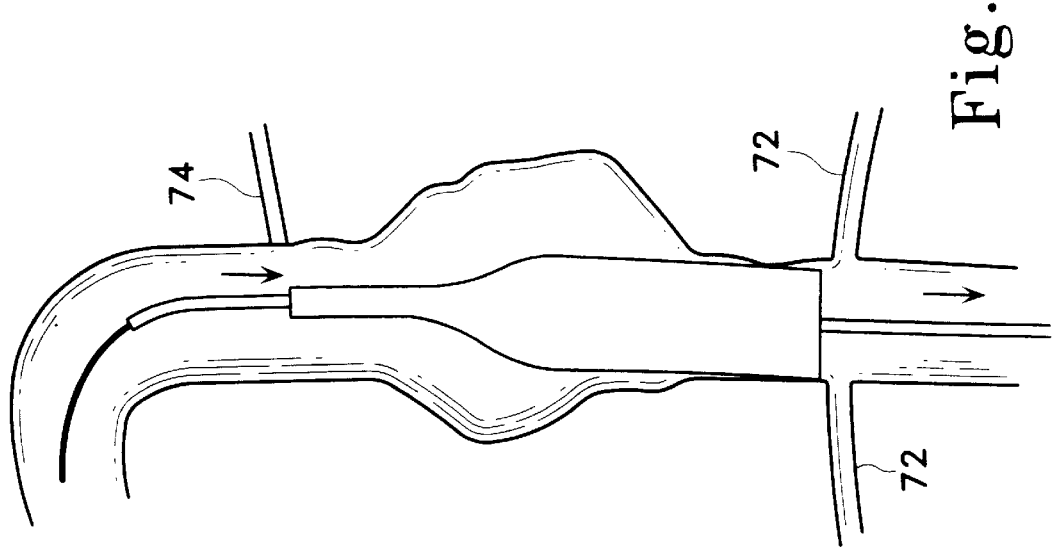

Once the proximal end is correctly located (FIG. 24), the stent graft is fully deployed, and the delivery catheter is removed (FIG. 25).

Throughout this application, various publications, patents and patent applications are referred by an identifying citation. The disclosures of these publications, patents and published patent applications are hereby incorporated by referenced into this application.

The above is a detailed description of a particular embodiment of the invention. The full scope of the invention is set out in the claims that follow and their equivalents. Accordingly, the claims and specification should not be construed to unduly narrow the full scope of protection to which the invention is entitled.

What is claimed is:

1. A process for making a stent graft comprising:
   (a) placing a graft member around a mandrel;
   (b) positioning an undulating stent member having an inner surface and an outer surface around said graft member; and
   (c securing said stent member to said graft member with a ribbon having multiple spaced apart strips, which ribbon is adhered to at least one of the inner and outer surfaces of said stent member, to form a stent-graft assembly.

2. The process according to claim 1 further comprising the step of:
   (a1) prior to step (a), placing a cushioning layer around the mandrel.

3. The process according to claim 1, wherein said securing step comprises helically wrapping the ribbon around the stent member whereby adjacent turns of the helically wrapper ribbon are spaced from one another and form said spaced apart strips.

4. The process according to claim 2, wherein said securing step comprises helically wrapping the ribbon around the stent whereby adjacent turns of the helically wrapper ribbon are spaced from one another.

5. The process according to claim 2 wherein the ribbon is bonded to an outer surface of the graft member.

6. The process according to claim 1 further comprising the step of:
   (d) placing a sheath around the assembly of step (c) to form a compressed assembly.

7. The process according to claim 6 further comprising the step of:
   (e) heating the assembly of step (d) to adhere the ribbon to the graft member.

8. The process according to claim 4 further comprising:
   (d) placing a tubular sheath having a longitudinal slit around the assembly of step (c); and
   (e) helically wrapping a film around the sheath to compress the assembly.

9. The processing according to claim 6 wherein the sheath includes a helical wrapping of PTFE film.

10. The stent-graft of claim 6 wherein one side of said ribbon has a coating of fluorinated ethylene propylene polymer.

* * * * *